(12) United States Patent
Ovaa et al.

(10) Patent No.: US 11,174,224 B2
(45) Date of Patent: Nov. 16, 2021

(54) CATHEPSIN INHIBITORS

(71) Applicant: ACADEMISCH ZIEKENHUIS LEIDEN (H.O.D.N. LUMC), Leiden (NL)

(72) Inventors: Huib Ovaa, Leiden (NL); Maria Wilhelmina Elisabeth Mons, Leiden (NL); Stan Van Boeckel, Leiden (NL)

(73) Assignee: ACADEMISCH ZIEKENHUIS LEIDEN (H.O.D.N. LUMC), Leiden (NL)

( * ) Notice: Subject to any disclaimer, the term of this patent is extended or adjusted under 35 U.S.C. 154(b) by 0 days.

(21) Appl. No.: 16/770,200

(22) PCT Filed: Dec. 5, 2018

(86) PCT No.: PCT/NL2018/050810
§ 371 (c)(1),
(2) Date: Jun. 5, 2020

(87) PCT Pub. No.: WO2019/112426
PCT Pub. Date: Jun. 13, 2019

(65) Prior Publication Data
US 2020/0385341 A1    Dec. 10, 2020

(30) Foreign Application Priority Data

Dec. 5, 2017 (NL) .................. 2020021
Sep. 3, 2018 (NL) .................. 2021544

(51) Int. Cl.
*C07C 317/14* (2006.01)
*C07C 237/22* (2006.01)
*C07C 237/06* (2006.01)
*A61P 19/10* (2006.01)
*C07C 275/40* (2006.01)
*C07C 237/28* (2006.01)

(52) U.S. Cl.
CPC ............ *C07C 317/14* (2013.01); *A61P 19/10* (2018.01); *C07C 237/06* (2013.01); *C07C 237/22* (2013.01); *C07C 237/28* (2013.01); *C07C 275/40* (2013.01)

(58) Field of Classification Search
None
See application file for complete search history.

(56) References Cited

FOREIGN PATENT DOCUMENTS

JP     2002145849    *  5/2002
WO     2003075836 A2   9/2003

OTHER PUBLICATIONS

Vidal-Albalat ("Chapter 6: Natural Products as Cathepsin Inhibitors" Studies in Natural Products Chemistry, vol. 50, 2016, http://dx.doi.org/10.1016/B978-0-444-63749-9.00006-2, p. 179-213) (Year: 2016).*

* cited by examiner

*Primary Examiner* — Amy C Bonaparte
(74) *Attorney, Agent, or Firm* — Nixon Peabody LLP; Ronald I. Eisenstein; Nicole D. Kling

(57) ABSTRACT

This invention relates to compounds that are useful as inhibitors, in particular as inhibitors of Cathepsin K (CatK), and to a method of inhibiting cathepsin activity, comprising administering a compound or formulation comprising a compound according to the invention.

20 Claims, 4 Drawing Sheets

CATHEPSIN INHIBITORS

CROSS-REFERENCE TO RELATED APPLICATIONS

This application is a 35 U.S.C. § 371 National Phase Entry Application of International Application No. PCT/NL2018/050810 filed Dec. 5, 2018, which claims benefit under 35 U.S.C. § 119(a) of NL Application Nos. 2020021 filed Dec. 5, 2017 and U.S. Pat. No. 2,021,544 filed Sep. 3, 2018, the contents of which are incorporated herein by reference in their entireties.

This invention relates to compounds that are useful as inhibitors, in particular as inhibitors of Cathepsin K (CatK).

BACKGROUND

Abnormal bone resorption is a factor in a number of disorders that affect humans and other vertebrates. Examples of these disorders include osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. Osteoporosis is of particular importance and in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture.

Osteoporosis is characterized by progressive loss of bone architecture and mineralization leading to the loss in bone strength and an increased fracture rate. The skeleton is constantly being remodeled by a balance between osteoblasts that lay down new bone and osteoclasts that breakdown, or resorb, bone. In some disease conditions and advancing age the balance between bone formation and resorption is disrupted; bone is removed at a faster rate. Such a prolonged imbalance of resorption over formation leads to weaker bone structure and a higher risk of fractures.

Bone resorption is primarily performed by osteoclasts, which are multinuclear giant cells. Osteoclasts resorb bone by forming an initial cellular attachment to bone tissue, followed by the formation of an extracellular compartment or lacunae. The lacunae are maintained at a low pH by a proton-ATP pump. The acidified environment in the lacunae allows for initial demineralization of bone followed by the degradation of bone proteins or collagen by proteases such as cysteine proteases (Delaisse, J. M. et al., 1980, Biochem J 192:365-368; Delaisse, J. et al., 1984, Biochem Biophys Res Commun:441-447; Delaisse, J. M. et al., 1987, Bone 8:305-313, which are hereby incorporated by reference in their entirety). Collagen constitutes 95% of the organic matrix of bone. Therefore, proteases involved in collagen degradation are an essential component of bone turnover, and as a consequence, the development and progression of osteoporosis.

Cathepsins belong to the papain superfamily of cysteine proteases. These proteases function in the normal physiological as well as pathological degradation of connective tissue. Cathepsins play a major role in intracellular protein degradation and turnover and remodeling. A number of cathepsins have been identified and sequenced from a number of sources. These cathepsins are naturally found in a wide variety of tissues.

Cathepsin K (CatK) is a cysteine protease that is mainly expressed in osteoclasts, and is the most important protease in bone degradation (V. Turk, V. Stoka, O. Vasiljeva, M. Renko, T. Sun, B. Turk, D. Turk, *Biochim. Biophys. Acta, Proteins Proteomics* 2012, 1824, 68, hereby incorporated by reference in its entirety). It has been implicated in diseases such as osteoporosis, rheumatoid arthritis and bone metastases, and its inhibition has been of interest for the past decade (D. Brömme, F. Lecaille, *Expert Opin. Invest. Drugs* 2009, 18, 585, hereby incorporated by reference in its entirety).

The most promising small molecule CatK inhibitor to date was Odanacatib (MK-0822 or ODN; see J. Y. Gauthier, et al., *Bioorg. Med. Chem. Lett.* 2008, 18, 923, hereby incorporated by reference in its entirety), a non-lysosomotropic inhibitor with a nitrile moiety as reversible covalent warhead that binds to catalytic Cys25. ODN has a high selectivity for CatK versus other Cathepsins, and only has to be taken once weekly because of its half-life of 66-93 h (S. A. Stoch, et al., *Clin. Pharmacol. Ther.* 2009, 86, 175, hereby incorporated by reference in its entirety). The development of ODN was, however, terminated after phase III clinical trials showed an increased stroke risk (A. Mullard, *Nat. Rev. Drug Discovery* 2016, 15, 669, hereby incorporated by reference in its entirety). ODN accordingly suffers from a number of limitations.

There is thus a general need to develop further treatments for abnormal bone resorption. An object of the invention is therefore to provide compounds that are useful in the treatment of abnormal bone resorption. Another object of the invention is to provide compounds that are useful as inhibitors of CatK. A further object of the invention is to provide methods for the treatment of abnormal bone resorption. Another object is to provide methods for the treatment of other diseases, such as bone metastases.

SUMMARY OF THE INVENTION

The invention provides compounds that are useful as inhibitors of cysteine proteases, such as CatK. In particular, the invention provides compounds that comprise an alkyne moiety that is believed to form an irreversible covalent bond with the active site cysteine of CatK.

In accordance with an aspect the present invention provides a compound of formula I:

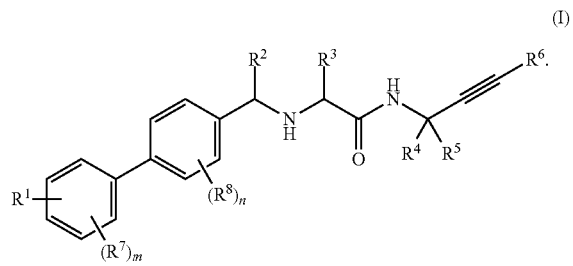

$R^1$ is —$S(O)_2R^a$, —$C(O)R^a$, —X, —H, —CN, —$C_1$-$C_6$ substituted or unsubstituted alkyl, —$C_3$-$C_6$ substituted or unsubstituted cycloalkyl, —$C_1$-$C_6$ alkoxy, —$C_3$-$C_6$ cycloalkoxy, —$NHC(O)R^a$, —$NHC(O)NHR^a$, —$C_2$-$C_5$ lactam, or —$C_1$-$C_4$ cyclourea. $R^1$ is located para or meta to the phenylene moiety. $R^2$ is —$C_1$-$C_4$ alkyl, —$C_1$-$C_4$ haloalkyl, or =O. $R^3$ is —$C_2$-$C_6$ alkyl, or —$C_2$-$C_6$ haloalkyl. $R^4$ and $R^5$ are independently selected from —H, —$C_1$-$C_3$ alkyl, or —$C_1$-$C_3$ haloalkyl; or $R^4$ and $R^5$ together with the carbon atom to which they are attached form a $C_3$-$C_6$ cycloalkyl, $C_3$-$C_6$ heterocycloalkyl, or $C_3$-$C_6$ cyclohaloalkyl. $R^6$ is —H, —Y, —$CH_3$, —$CY_3$, —$CHY_2$, or —$CH_2Y$. $R^7$ is —H, —X, —CN, —$C_1$-$C_4$ alkyl, —$C_1$-$C_4$ haloalkyl, or —$C_1$-$C_3$ alkoxy. $R^8$ is —H, —X, —CN, —$C_1$-$C_4$ alkyl, —$C_1$-$C_4$ haloalkyl, or —$C_1$-$C_3$ alkoxy. $R^6$ is —H, —$C_1$-$C_6$ substituted or unsubstituted alkyl, —$NH_2$, or —$NR^9R^{10}$. $R^9$ and $R^{10}$ are independently selected from —H, $C_3$ alkyl, or —$C_1$-$C_3$ haloalkyl; or $R^9$ and $R^{10}$ together with the carbon atom to which they are attached form a $C_3$-$C_6$ cycloalkyl, $C_3$-$C_6$ heterocycloalkyl, or $C_3$-$C_6$ cyclohaloalkyl. Each X is independently selected from —F, —Cl, —Br or —I. Y is —F, —Cl, —Br, or —I. m is 0, 1, 2, 3, or 4. n is 0, 1 or 2. The compound may also be a pharmaceutically acceptable salt, stereoisomer, or prodrug of a compound of formula I.

Another aspect of the invention provides a formulation, comprising a compound of the invention. The formulation may be a pharmaceutical formulation. The formulation may also comprise a pharmaceutically acceptable carrier.

Another aspect provides a compound of the invention or formulation of the invention for use as a medicament.

A further aspect provides a compound of the invention or formulation of the invention for use treating a disease selected from osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy or multiple myeloma.

An aspect provides a compound or formulation of the invention for use in treating a cathepsin dependent condition, e.g. a condition that may be treated by the administration of a cathepsin inhibitor. The cathepsin dependent condition may be a cathepsin K dependent condition.

Another aspect provides a method of treating a disease selected from osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy or multiple myeloma in a patient in need thereof by administering an effective amount of a compound of the invention to the patient. The disease may be osteoporosis.

A further aspect provides a method of inhibiting cathepsin activity, comprising administering a compound of the invention. The administering may be to a patient, or may be performed in vitro, for example to a cell culture. The method may be a method of inhibiting cathepsin K activity. A related aspect provides use of a compound of the invention to inhibit cathepsin activity, e.g. to inhibit cathepsin K activity.

The invention will now be described further by reference to the following examples and figures. These are not intended to be limiting but merely exemplary of the invention.

BRIEF DESCRIPTION OF THE DRAWINGS

Embodiments of the invention are further described hereinafter with reference to the accompanying drawings, in which.

DETAILED DESCRIPTION OF THE INVENTION

Figure 1:
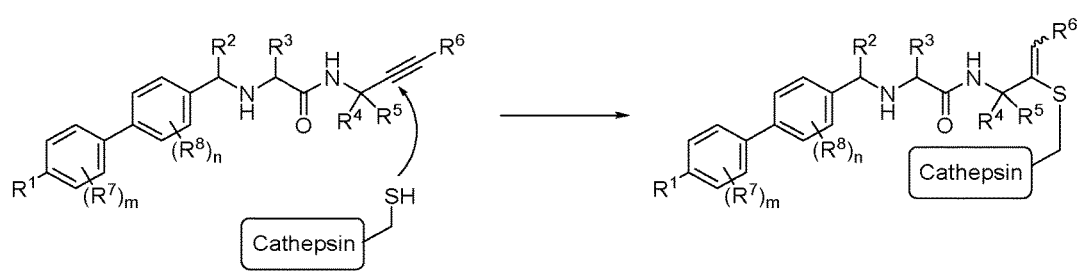
FIG. 1 is a reaction scheme, illustrating how the terminal alkyne moiety of a compound of the invention acts as an 'inert' electrophile for thiol-alkyne addition as an irreversible covalent small molecule inhibitor of cysteine protease CatK.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

All publications, patent applications, patents, and other references mentioned herein are incorporated by reference in their entirety. In case of conflict, the present specification, including definitions, will control.

Definitions

The following explanations of terms and methods are provided to better describe the present disclosure and to guide those of ordinary skill in the art in the practice of the present disclosure.

The invention concerns amongst other things the treatment of a disease. The term "treatment", and the therapies encompassed by this invention, include the following and combinations thereof: (1) hindering, e.g. delaying initiation and/or progression of, an event, state, disorder or condition, for example arresting, reducing or delaying the development of the event, state, disorder or condition, or a relapse thereof in case of maintenance treatment or secondary prophylaxis, or of at least one clinical or subclinical symptom thereof; (2) preventing or delaying the appearance of clinical symptoms of an event, state, disorder or condition developing in an animal (e.g. human) that may be afflicted with or predisposed to the state, disorder or condition but does not yet experience or display clinical or subclinical symptoms of the state, disorder or condition; and/or (3) relieving and/or curing an event, state, disorder or condition (e.g., causing regression of the event, state, disorder or condition or at least one of its clinical or subclinical symptoms, curing a patient or putting a patient into remission). The benefit to a patient to be treated may be either statistically significant or at least perceptible to the patient or to the physician. It will be understood that a medicament will not necessarily produce a clinical effect in each patient to whom it is administered; thus, in any individual patient or even in a particular patient population, a treatment may fail or be successful only in part, and the meanings of the terms "treatment", "prophylaxis" and "inhibitor" and of cognate terms are to be understood accordingly. The compositions and methods described herein are of use for therapy and/or prophylaxis of the mentioned conditions.

The term "prophylaxis" includes reference to treatment therapies for the purpose of preserving health or inhibiting or delaying the initiation and/or progression of an event, state, disorder or condition, for example for the purpose of reducing the chance of an event, state, disorder or condition occurring. The outcome of the prophylaxis may be, for example, preservation of health or delaying the initiation and/or progression of an event, state, disorder or condition. It will be recalled that, in any individual patient or even in a particular patient population, a treatment may fail, and this paragraph is to be understood accordingly.

The term "inhibit" (and "inhibiting") includes reference to delaying, stopping, reducing the incidence of, reducing the risk of and/or reducing the severity of an event, state, disorder or condition. Inhibiting an event, state, disorder or condition may therefore include delaying or stopping initiation and/or progression of such, and reducing the risk of such occurring. The products of the disclosure may be used to inhibit one or more proteases and thereby inhibit osteoporosis and/or other events, disorders and/or conditions which are disclosed herein. For example, the compounds of the invention may inhibit CatK.

An "inhibitor" is a molecule that binds to an enzyme and decreases its activity. An "irreversible inhibitor" is an inhibitor where the binding involves a chemical reaction, e.g. formation of a covalent bond between the molecule and enzyme. The compounds of the invention may act as irreversible inhibitors of CatK.

The terms "alkyl" as used herein include reference to a straight or branched chain alkyl moiety having 1, 2, 3, 4, 5, 6, 7, 8, 9 or 10 carbon atoms. The term includes reference to, for example, methyl, ethyl, propyl (n-propyl or isopropyl), butyl (n-butyl, sec-butyl or tert-butyl), pentyl, hexyl and the like. In particular, alkyl may be a "$C_1$-$C_4$ alkyl", i.e. an alkyl having 1, 2, 3 or 4 carbon atoms; or a "$C_1$-$C_6$ alkyl", i.e. an alkyl having 1, 2, 3, 4, 5 or 6 carbon atoms; or a "$C_1$-$C_3$ alkyl", i.e. an alkyl having 1, 2 or 3 carbon atoms.

The term "lower alkyl" includes reference to alkyl groups having 1, 2, 3 or 4 carbon atoms.

The term "cycloalkyl" as used herein includes reference to an alicyclic moiety having 3, 4, 5 or 6 carbon atoms. The group may be a bridged or polycyclic ring system. More often cycloalkyl groups are monocyclic. This term includes reference to groups such as cyclopropyl, cyclobutyl, cyclopentyl, cyclohexyl and the like.

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. For example, a heterocycolalkyl may comprise 3, 4, or 5 ring carbon atoms and 1 or 2 ring heteroatoms selected from nitrogen and oxygen. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like.

The terms "halo" or "halogen" as used herein includes reference to F, Cl, Br or I, for example F, Cl or Br. In a particular class of embodiments, halogen is F or Cl, of which F is more common.

The term "haloalkyl" refers to an alkyl group where one or more hydrogen atoms are substituted by a corresponding number of halogens. An exemplary haloalkyl group is trifluoromethyl. Another exemplary haloalkyl group is 2-fluoro-2-methylpropyl.

The term "alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms, e.g. 1, 2 or 3 carbon atoms. This term includes reference to, for example, methoxy, ethoxy, propoxy, isopropoxy, butoxy, tert-butoxy, pentoxy, hexoxy and the like. The term "lower alkoxy" includes reference to alkoxy groups having 1, 2, 3 or 4 carbon atoms.

The term "haloalkoxy" as used herein refers to an alkoxy group where one or more hydrogen atoms are substituted by a corresponding number of halogens.

The term "substituted" as used herein in reference to a moiety means that one or more, especially up to 5, more especially 1, 2 or 3, of the hydrogen atoms in said moiety are replaced independently of each other by the corresponding number of the described substituents. Unless otherwise specified, exemplary substituents include —OH, —CN, —NH$_2$, =O, -halo, —C$_1$-C$_6$ alkyl, —C$_2$-C$_6$ alkenyl, —C$_1$-C$_6$ haloalkyl, —C$_1$-C$_6$ haloalkoxy and —C$_2$-C$_6$ haloalkenyl, —C$_1$-C$_6$ alkylcarboxylic acid (e.g. —CH$_3$COOH or —COOH). Where the substituent is a —C$_1$-C$_6$ alkyl or —C$_1$-C$_6$ haloalkyl, the C$_1$-C$_6$ chain is optionally interrupted by an ether linkage (—O—) or an ester linkage (—C(O)O—). Exemplary substituents for a substituted alkyl may include —OH, —CN, —NH$_2$, =O, -halo, —CO$_2$H, —C$_1$-C$_6$ haloalkyl, —C$_1$-C$_6$ haloalkoxy and —C$_2$-C$_6$haloalkenyl, —C$_1$-C$_6$ alkylcarboxylic acid (e.g. —CH$_3$COOH or —COOH). For example, exemplary substituents for an alkyl may include —OH, —CN, —NH$_2$, =O, -halo.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled person.

Where steric issues determine placement of substituents on a group, the isomer having the lowest conformational energy may be preferred.

Where a compound, moiety, process or product is described as "optionally" having a feature, the disclosure includes such a compound, moiety, process or product having that feature and also such a compound, moiety, process or product not having that feature. Thus, when a moiety is described as "optionally substituted", the disclosure comprises the unsubstituted moiety and the substituted moiety.

Where two or more moieties are described as being "independently" or "each independently" selected from a list of atoms or groups, this means that the moieties may be the same or different. The identity of each moiety is therefore independent of the identities of the one or more other moieties.

The term "pharmaceutically acceptable" as used herein includes reference to those compounds, materials, compositions, and/or dosage forms which are, within the scope of sound medical judgment, suitable for use in contact with the tissues of human beings or animals without excessive toxicity, irritation, allergic response, or other problem or complication, commensurate with a reasonable benefit/risk ratio. This term includes acceptability for both human and veterinary purposes.

The term "pharmaceutical formulation" as used herein includes reference to a formulation comprising at least one active compound and optionally one or more additional pharmaceutically acceptable ingredients, for example a pharmaceutically acceptable carrier. Where a pharmaceutical formulation comprises two or more active compounds, or comprises at least one active compound and one or more additional pharmaceutically acceptable ingredients, the pharmaceutical formulation is also a pharmaceutical composition. Unless the context indicates otherwise, all references to a "formulation" herein are references to a pharmaceutical formulation.

The term "product" or "product of the invention" as used herein includes reference to any product containing a compound of the present invention. In particular, the term product relates to compositions and formulations containing a compound of the present invention, such as a pharmaceutical composition, for example.

The term "therapeutically effective amount" as used herein refers to an amount of a drug, or pharmaceutical agent that, within the scope of sound pharmacological judgment, is calculated to (or will) provide a desired therapeutic response in a mammal (animal or human). The therapeutic response may for example serve to cure, delay the progression of or prevent a disease, disorder or condition.

The term "prodrug" as used herein represents compounds which are transformed in vivo to the parent compound, for example, by hydrolysis in blood. An example of such a prodrug is a pharmaceutically acceptable ester of a carboxylic acid. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987; H Bundgaard, ed, Design of Prodrugs, Elsevier, 1985; and Judkins, et al. Synthetic Communications, 26(23), 4351-4367 (1996); and The organic chemistry of drug design and drug action by Richard B Silverman in particular pages 497 to 546; each of which is incorporated herein by reference.

Compounds

In one aspect, the invention provides compounds of formula I as previously described or a pharmaceutically acceptable salt, stereoisomer, or prodrug thereof. In embodiments, one or more of $R^1$, $R^2$, $R^3$, $R^4$, $R^5$, $R^6$, $R^7$, $R^8$, X, Y, m and n are as described in the following paragraphs:

In an embodiment, $R^1$ is $-S(O)_2R^a$, $-C(O)R^a$, $-X$, $-H$, $-CN$, $-C_1-C_6$ (e.g. $-C_1-C_4$) substituted or unsubstituted alkyl, or $-C_3-C_6$ (e.g. $-C_3-C_4$) substituted or unsubstituted cycloalkyl, $-C_1-C_6$ alkoxy (e.g. $-C_1-C_4$ alkoxy), $-C_3-C_6$ cycloalkoxy (e.g. $-C_3-C_4$ cycloalkyloxy), $-NHC(O)R^a$, $-NHC(O)NHR^a$, $-C_2-C_5$ lactam (e.g. $-C_2-C_3$ lactam), or $-C_1-C_4$ cyclourea ($-C_1-C_2$ cyclourea). $R^1$ may be $-S(O)_2R^a$, $-C(O)R^a$, $-X$, $-C_1-C_6$ substituted or unsubstituted alkyl, or $-C_3-C_6$ substituted or unsubstituted cycloalkyl. $R^1$ may be $-S(O)_2R^a$, $-C(O)R^a$, $-X$, $-H$, $-CN$, $-C_1-C_6$ unsubstituted alkyl, or $-C_3-C_6$ unsubstituted cycloalkyl. $R^1$ may be $-S(O)_2R^a$, $-C(O)R^a$, $-X$, $-C_1-C_6$ unsubstituted alkyl, or $-C_3-C_6$ unsubstituted cycloalkyl. $R^1$ may be $-S(O)_2R^a$, $-X$, $-C_1-C_6$ unsubstituted alkyl, or $-C_3-C_6$ unsubstituted cycloalkyl. $R^1$ may be $-S(O)_2R^a$, $-C(O)R^a$, $-C_1-C_6$ substituted or unsubstituted alkyl, or $-C_3-C_6$ substituted or unsubstituted cycloalkyl, $-C_1-C_6$ alkoxy, $-C_3-C_6$ cycloalkoxy, $-NHC(O)R^a$, $-NHC(O)NHR^a$, $-C_2-C_5$ lactam. $R^1$ may be $-S(O)_2R^a$, $-C(O)R^a$, $-NHC(O)R^a$, $-NHC(O)NHR^a$. $R^1$ may be $-S(O)_2R^a$. $R^1$ may be $-C(O)R^a$. $R^1$ may be $-X$. $R^1$ may be $-H$. $R^1$ may be $-CN$. $R^1$ may be $-C_1-C_6$ substituted or unsubstituted alkyl. $R^1$ may be $-C_1-C_4$ substituted or unsubstituted alkyl. $R^1$ may be or $-C_3-C_6$ (e.g. $-C_3-C_4$) unsubstituted cycloalkyl. $R^1$ may be alkoxy (e.g. $-C_1-C_4$ alkoxy). $R^1$ may be $-C_3-C_6$ cycloalkoxy (e.g. $-C_3-C_4$ cycloalkyloxy). $R^1$ may be $-NHC(O)R^a$. $R^1$ may be $-NHC(O)NHR^a$. $R^1$ may be $-C_2-C_5$ lactam (e.g. $-C_2-C_3$ lactam). $R^1$ may be $-C_1-C_4$ cyclourea ($-C_1-C_2$ cyclourea).

Where $R^1$ is a substituted $-C_1-C_6$ (e.g. $-C_1-C_4$) substituted alkyl, 1, 2 or 3 of the hydrogen atoms of the alkyl may be substituted and/or the alkyl chain may be interrupted by an ether linkage ($-O-$) or an ester linkage ($-C(O)O-$). Each substituent may be independently selected from $-OH$, $-CN$, $-NH_2$, $=O$, -halo, $-CO_2H$, haloalkyl, $-C_1-C_6$ haloalkoxy and $-C_2-C_6$haloalkenyl, $-C_1-C_6$ alkylcarboxylic acid (e.g. $-CH_3COOH$ or $-COOH$). Where $R^1$ is a substituted $-C_3-C_6$ (e.g. $-C_3-C_4$) cycloalkyl, 1, 2 or 3 of the hydrogen atoms of the cycloalkyl may be substituted and/or the cycloalkyl ring may be interrupted by an ether linkage ($-O-$) or an ester linkage ($-C(O)O-$). Each substituent may be independently selected from $-OH$, $-CN$, $-NH_2$, $=O$, -halo, $-CO_2H$, $-C_1-C_6$ haloalkyl, $-C_1-C_6$ haloalkoxy and $-C_2-C_6$haloalkenyl, $-C_1-C_6$ alkylcarboxylic acid (e.g. $-CH_3COOH$ or $-COOH$).

$R^1$ may be located para to the phenylene moiety. $R^1$ may be located meta to the phenylene moiety.

In an embodiment, $R^2$ is $-C_1-C_4$ alkyl, or $-C_1-C_4$ haloalkyl. $R^2$ may be $-C_1-C_4$ haloalkyl. $R^2$ may be $-C_1-C_2$ haloalkyl. $R^2$ may be $-C_1-C_4$ fluoroalkyl. $R^2$ may be $-C_1-C_2$ fluoroalkyl. $R^2$ may be $-C_1$ haloalkyl, e.g. $-CH_2F$, $-CHF_2$ or $-CF_3$. $R^2$ may be $-CF_3$. In an embodiment, $R^2$ is $-C_1-C_4$ alkyl. $R^2$ may be $-C_1-C_2$ alkyl. $R^2$ may be $-CH_3$.

In an embodiment, $R^3$ is $-C_2-C_6$ haloalkyl. For example, $R^3$ may be a $-C_3$ haloalkyl, $-C_4$ haloalkyl, or $-C_5$ haloalkyl. $R^3$ may be a $C_4$ haloalkyl. $R^3$ may be a $-C_2-C_6$ fluoroalkyl. For example, $R^3$ may be a —$C_3$ fluoroalkyl, fluoroalkyl, or —$C_5$ fluoroalkyl. $R^3$ may be a $C_4$ fluoroalkyl. $R^3$ may be —$CH_2C(CH_3)_2F$.

In an embodiment, $R^4$ is —H, —$C_1$-$C_2$ alkyl, or —$C_1$-$C_2$ haloalkyl. $R^4$ may be —H, —$CH_3$, or —$CH_2CH_3$. $R^4$ may be —H or —$CH_3$. $R^4$ may be —H. In an embodiment, $R^5$ is —H, —$C_1$-$C_2$ alkyl, or —$C_1$-$C_2$ haloalkyl. $R^5$ may be —H, —$CH_3$, or —$CH_2CH_3$. $R^5$ may be —H or —$CH_3$. $R^5$ may be —H. In an embodiment, $R^4$ is —H and $R^5$ is —$CH_3$. In an embodiment, $R^4$ is —H and $R^5$ is —H. In an embodiment, $R^4$ and $R^5$ together with the carbon atom to which they are attached form a $C_3$-$C_6$ cycloalkyl, $C_3$-$C_6$ heterocycloalkyl, or $C_3$-$C_6$ cyclohaloalkyl. $R^4$ and $R^5$ together with the carbon atom to which they are attached may form a $C_3$-$C_6$ cycloalkyl or $C_3$-$C_6$ cyclohaloalkyl. $R^4$ and $R^5$ together with the carbon atom to which they are attached may form a $C_3$ or $C_4$ cycloalkyl (e.g. a $C_3$ cycloalkyl). $R^4$ and $R^5$ together with the carbon atom to which they are attached may form a $C_3$-$C_6$ heterocycloalkyl (for example a tetrohydrofuranyl, piperidinyl, or morpholinyl; e.g. a morpholinyl). $R^4$ and $R^5$ together with the carbon atom to which they are attached may form a $C_3$ or $C_4$ cyclohaloalkyl (e.g. a $C_3$ cyclohaloalkyl).

In an embodiment, $R^6$ is —H, —$CH_3$, —$CY_3$, —$CHY_2$, or —$CH_2Y$. $R^6$ may be —H or —$CH_3$. $R^6$ may be —H or —Y. $R^6$ may be —H. $R^6$ may be —Y. $R^6$ may be —$CH_3$. $R^6$ may be —$CH_2Y$. $R^6$ may be —$CHY_2$. $R^6$ may be —$CY_3$.

In an embodiment, each $R^7$ is independently selected from —H, —X, —CN, or —$C_1$-$C_4$ alkyl. Each $R^7$ may be independently selected from —H, —X, or —CN, or —$C_1$-$C_4$ alkyl. Each $R^7$ may be independently selected from —X, or —$C_1$-$C_4$ alkyl. Each $R^7$ may be —X. Each $R^7$ may be the same. Each $R^7$ may be different.

In an embodiment, each $R^8$ is independently selected from —H, —X, —CN, or —$C_1$-$C_4$ alkyl. Each $R^8$ is independently selected from —H, —X, or —CN, or —$C_1$-$C_4$ alkyl. Each $R^8$ may be independently selected from —X, or —$C_1$-$C_4$ alkyl. Each $R^8$ may be —X. Each $R^8$ may be the same. Each $R^8$ may be different. Where each $R^7$ is the same and each $R^8$ is the same, $R^7$ may be the same as $R^8$.

In an embodiment, $R^9$ is —H, —$C_1$-$C_2$ alkyl, or —$C_1$-$C_2$ haloalkyl. $R^9$ may be —H, —$CH_3$, or —$CH_2CH_3$. $R^9$ may be —H or —$CH_3$. $R^9$ may be —H. In an embodiment, $R^{10}$ is —H, —$C_1$-$C_2$ alkyl, or —$C_1$-$C_2$ haloalkyl. $R^{10}$ may be —H, —$CH_3$, or —$CH_2CH_3$. $R^{10}$ may be —H or —$CH_3$. $R^{10}$ may be —H. In an embodiment, $R^9$ is —H and $R^{10}$ is —$CH_3$. In an embodiment, $R^9$ is —H and $R^{10}$ is —H. In an embodiment, $R^9$ and $R^{10}$ together with the carbon atom to which they are attached form a $C_3$-$C_6$ cycloalkyl, $C_3$-$C_6$ heterocycloalkyl, or $C_3$-$C_6$ cyclohaloalkyl. $R^9$ and $R^{10}$ together with the carbon atom to which they are attached may form a $C_3$-$C_6$ cycloalkyl or $C_3$-$C_6$ cyclohaloalkyl. $R^9$ and $R^{10}$ together with the carbon atom to which they are attached may form a $C_3$ or $C_4$ cycloalkyl (e.g. a $C_3$ cycloalkyl). $R^9$ and $R^{10}$ together with the carbon atom to which they are attached may form a $C_3$-$C_6$ heterocycloalkyl (for example a tetrohydrofuranyl, piperidinyl, or morpholinyl; e.g. a morpholinyl). $R^9$ and $R^{10}$ together with the carbon atom to which they are attached may form a $C_3$ or $C_4$ cyclohaloalkyl (e.g. a $C_3$ cyclohaloalkyl).

In an embodiment, $R^a$ is selected from —H, —$C_1$-$C_6$ (e.g. —$C_1$-$C_4$) substituted or unsubstituted alkyl, or —$NH_2$. In an embodiment, $R^a$ is selected from —H, —$C_1$-$C_6$ (e.g. —$C_1$-$C_4$) substituted or unsubstituted alkyl. $R^a$ is —H, —$CH_3$, or —$CH_2CH_3$. In an embodiment, $R^a$ is —$CH_3$, or —$CH_2CH_3$. $R^a$ may be —$CH_3$. $R^a$ may be —H. $R^a$ may be —$NH_2$ or —$NR^9R^{10}$ (e.g. $R^a$ may be —$NH_2$).

In an embodiment, each X is independently selected from —F, —Cl, —Br. X may be —F. X may be —Cl. X may be —Br. X may by —I. Each X may be the same. Each X may be different.

In an embodiment, each Y is independently selected from —F, —Cl, —Br. Y may be —F. Y may be —Cl. Y may be —Br. Y may by —I. Each Y may be the same. Each Y may be different.

In an embodiment, m is 0, 1, or 2. m may be 0 or 1, e.g. m may be 0. In an embodiment, n is 0, or 1, e.g. n may be 0. In an embodiment, m is 0 or 1 and n is 0. For example, m may be 1 and n may be 0. For example, m may be 0 and n may be 0.

In an embodiment, $R^1$ is —$S(O)_2R^a$ and $R^a$ is —$C_1$-$C_4$ alkyl. $R^2$ is —$C_1$-$C_4$ alkyl, or —$C_1$-$C_4$haloalkyl. $R^3$ is —$C_2$-$C_6$ alkyl, or —$C_2$-$C_6$ haloalkyl. $R^4$ and $R^5$ are independently selected from —H, —$C_1$-$C_3$ alkyl, or —$C_1$-$C_3$ haloalkyl; or $R^4$ and $R^5$ together with the carbon atom to which they are attached form a $C_3$-$C_6$ cycloalkyl or $C_3$-$C_6$ cyclohaloalkyl. $R^6$ is —H, —X, —$CH_3$, —$CX_3$, —$CHX_2$, —$CH_2X$; X is —F, —Cl, —Br or —I. Each of m and n are 0.

In an embodiment, $R^1$ is —$S(O)_2R^a$, —$C(O)R^a$, —X, —H, —CN, —$C_1$-$C_6$ substituted or unsubstituted alkyl, or —$C_3$-$C_6$ substituted or unsubstituted cycloalkyl, —$C_1$-$C_6$ alkoxy, —$C_3$-$C_6$ cycloalkoxy, —$NHC(O)R^a$, —$NHC(O)NHR^a$, —$C_2$-$C_5$ lactam, or —$C_1$-$C_4$ cyclourea. $R^1$ is located para or meta to the phenylene moiety. $R^2$ is —$C_1$-$C_4$ alkyl, —$C_1$-$C_4$ haloalkyl, or =O. $R^3$ is —$C_2$-$C_6$ alkyl, or —$C_2$-$C_6$ haloalkyl. $R^4$ and $R^5$ are independently selected from —H, —$C_1$-$C_3$ alkyl, or —$C_1$-$C_3$ haloalkyl; or $R^4$ and $R^5$ together with the carbon atom to which they are attached form a $C_3$-$C_6$ cycloalkyl, $C_3$-$C_6$ heterocycloalkyl, or $C_3$-$C_6$ cyclohaloalkyl. $R^6$ is —H, —$CH_3$, —$CY_3$, —$CHY_2$, or —$CH_2Y$. $R^7$ is —H, —X, —CN, —$C_1$-$C_4$ alkyl, —$C_1$-$C_4$ haloalkyl, or —$C_1$-$C_3$ alkoxy. $R^8$ is —H, —X, —CN, —$C_1$-$C_4$ alkyl, —$C_1$-$C_4$ haloalkyl, or —$C_1$-$C_3$ alkoxy. Each $R^a$ is independently selected from —H, —$C_1$-$C_6$ substituted or unsubstituted alkyl, —$NH_2$, or —$NR^9R^{10}$. $R^9$ and $R^{10}$ are independently selected from —H, —$C_1$-$C_3$ alkyl, or —$C_1$-$C_3$ haloalkyl; or $R^9$ and $R^{10}$ together with the carbon atom to which they are attached form a $C_3$-$C_6$ cycloalkyl, $C_3$-$C_6$ heterocycloalkyl, or $C_3$-$C_6$ cyclohaloalkyl. Each X is independently selected from —F, —Cl, —Br or —I. Y is —F, —Cl, —Br, or —I. m is 0, 1, 2, 3, or 4. n is 0, 1 or 2.

In an embodiment, $R^1$ is —$S(O)_2R^a$, —$C(O)R^a$, —X, —$C_1$-$C_6$ substituted or unsubstituted alkyl, or —$C_3$-$C_6$ substituted or unsubstituted cycloalkyl. $R^2$ is —$C_1$-$C_4$ alkyl, —$C_1$-$C_4$ haloalkyl, or =O. $R^3$ is —$C_2$-$C_6$ alkyl, or —$C_2$-$C_6$ haloalkyl. $R^4$ and $R^5$ are independently selected from —H, —$C_1$-$C_3$ alkyl, or —$C_1$-$C_3$ haloalkyl; or $R^4$ and $R^5$ together with the carbon atom to which they are attached form a $C_3$-$C_6$ cycloalkyl or $C_3$-$C_6$ cyclohaloalkyl. $R^6$ is —H, —Y, —$CH_3$, —$CY_3$, —$CHY_2$, or —$CH_2Y$. $R^7$ is —X, —$C_1$-$C_4$ alkyl, or —$C_1$-$C_4$ haloalkyl. $R^8$ is —X, —$C_1$-$C_4$ alkyl, or —$C_1$-$C_4$ haloalkyl. $R^a$ is —H, —$C_1$-$C_6$ substituted or unsubstituted alkyl, or —$NH_2$. Each X is independently selected from —F, —Cl, —Br or —I. Y is —F, —Cl, —Br, or —I. m is 0, 1, 2, 3, or 4. n is 0, 1 or 2.

In an embodiment, $R^1$ is —$S(O)_2R^a$, —$C(O)R^a$, —X, —$C_1$-$C_6$ substituted or unsubstituted alkyl, or —$C_3$-$C_6$ substituted or unsubstituted cycloalkyl. $R^2$ is —$C_1$-$C_4$ alkyl, —$C_1$-$C_4$ haloalkyl, or =O. $R^3$ is —$C_2$-$C_6$ alkyl, or —$C_2$-$C_6$ haloalkyl. $R^4$ and $R^5$ are independently selected from —H, —$C_1$-$C_3$ alkyl, or —$C_1$-$C_3$ haloalkyl; or $R^4$ and $R^5$ together with the carbon atom to which they are attached form a $C_3$-$C_6$ cycloalkyl or $C_3$-$C_6$ cyclohaloalkyl. $R^6$ is —H, —CH$_3$, —CY$_3$, —CHY$_2$, or —CH$_2$Y. R$^7$ is —X, —C$_1$-C$_4$ alkyl, or —C$_1$-C$_4$ haloalkyl. R$^8$ is —X, —C$_1$-C$_4$ alkyl, or —C$_1$-C$_4$ haloalkyl. R$^a$ is —H, —C$_1$-C$_6$ substituted or unsubstituted alkyl, or —NH$_2$. Each X is independently selected from —F, —Cl, —Br or —I. m is 0, 1, 2, 3, or 4. n is 0, 1 or 2.

In an embodiment, the compound is a compound of formula II:

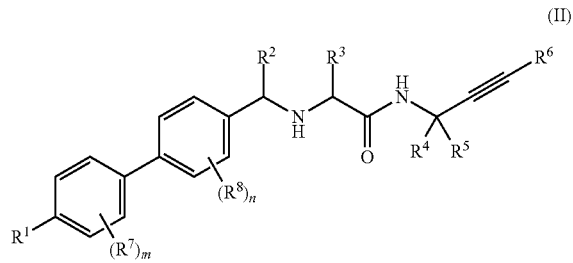

(II)

or a pharmaceutically acceptable salt, or prodrug thereof. R$^1$, R$^2$, R$^3$, R$^4$, R$^5$, R$^6$, R$^7$, R$^8$, m and n are as defined elsewhere in the present disclosure.

In an embodiment, the compound is a compound of formula IIa:

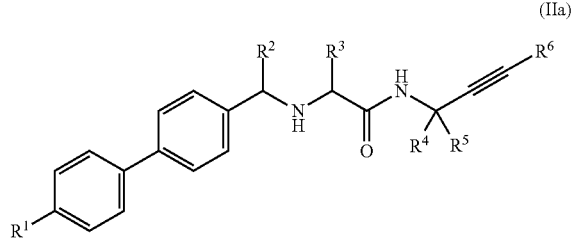

(IIa)

or a pharmaceutically acceptable salt, or prodrug thereof. R$^1$, R$^2$, R$^3$, R$^4$, R$^5$ and R$^6$ are as defined elsewhere in the present disclosure.

In an embodiment, the compound is a compound of formula IIb:

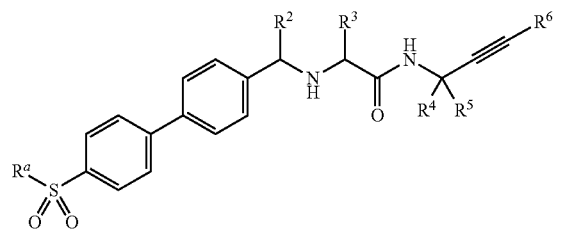

(IIb)

or a pharmaceutically acceptable salt, or prodrug thereof. R$^2$, R$^3$, R$^4$, R$^5$, R$^6$ and R$^a$ are as defined elsewhere in the present disclosure.

In an embodiment, the compound is a compound of formula III:

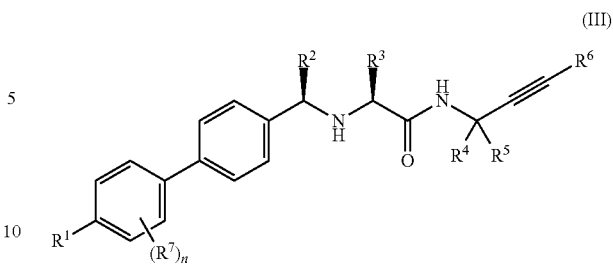

(III)

or a pharmaceutically acceptable salt, or prodrug thereof. R$^1$, R$^2$, R$^3$, R$^4$, R$^5$, R$^6$, R$^7$, R$^8$, m and n are as defined elsewhere in the present disclosure.

In an embodiment, the compound is a compound of formula IIIa:

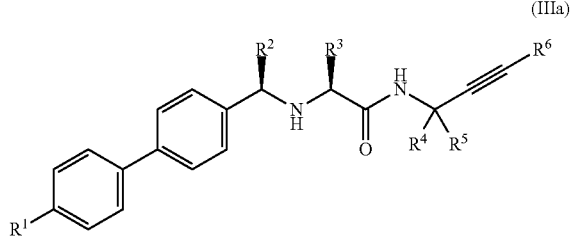

(IIIa)

or a pharmaceutically acceptable salt, or prodrug thereof. R$^1$, R$^2$, R$^3$, R$^4$, R$^5$ and R$^6$ are as defined elsewhere in the present disclosure.

In an embodiment, the compound is a compound of formula IIIb:

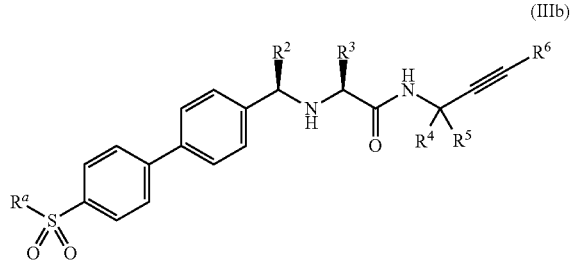

(IIIb)

or a pharmaceutically acceptable salt, or prodrug thereof. R$^2$, R$^3$, R$^4$, R$^5$, R$^6$ and R$^a$ are as defined elsewhere in the present disclosure.

In an embodiment, the compound is selected from:

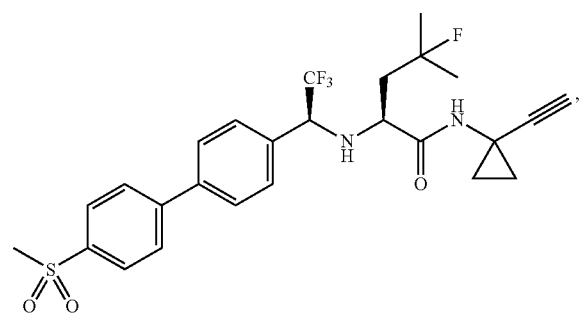

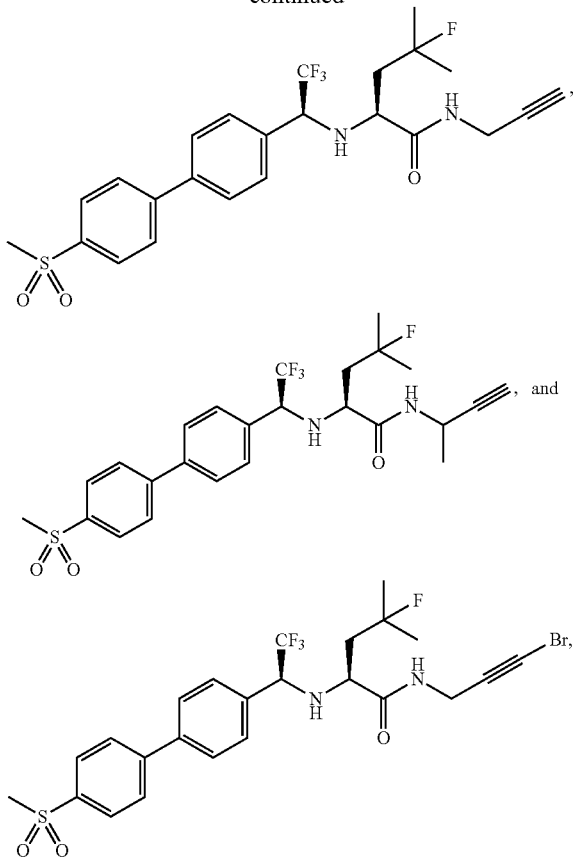

or a pharmaceutically acceptable salt or prodrug thereof.

In embodiments, compounds of the invention provide selective irreversible inhibition of CatK.

Uses

The Compounds of the invention are inhibitors of cysteine proteases. Compounds of the invention comprise an alkyne that acts as a latent electrophile. In embodiments, the 'inert' (or latent) alkyne moiety of the compound forms an irreversible covalent bond with the active site cysteine of a protease. The protease may be a cathepsin. For example, the protease may be CatK. FIG. 1 provides a reaction scheme illustrating how the terminal alkyne moiety of a compound of the invention acts as an 'inert' electrophile for thiol-alkyne addition as an irreversible covalent small molecule inhibitor of cysteine protease CatK.

Inhibition of Cathepsin K in osteoclasts results in diminished bone resorption activity of osteoclasts. It is believed that bone resorption activity may, however, be slowly regained after discontinuation of the treatment as a result of de novo Cathepsin K expression. For example, with compounds in the present invention, significant bone resorption activity may be regained after 9 days. Significant bone resorption activity may be at least 60% of the uninhibited activity (i.e. activity observed in negative control situation).

In compounds of the invention, the alkyne moiety is believed to act as a latent electrophile, which does not show indiscriminate thiol reactivity. This provides advantages compared to other covalent irreversible electrophiles incorporated into compounds, which typically show indiscriminate thiol reactivity. For example, compounds of the invention should have a reduced risk of significant (e.g. debilitating or lethal) side effects. Known irreversible inhibitors have typically been developed to treat cancer, and are associated with an increased risk of adverse effects due to indiscriminate thiol binding. The present compounds show a reduced level of indiscriminate binding (e.g. minimal or no indiscriminate binding) and are therefore expected to have a lower risk of adverse effects.

The compounds of the present invention are inhibitors of cathepsins and are therefore useful to treat or prevent cathepsin dependent diseases or conditions in mammals, preferably humans. Specifically, the compounds of the present invention are inhibitors of Cathepsin K and are therefore useful to treat or prevent Cathepsin K dependent diseases or conditions in mammals, preferably humans.

"Cathepsin dependent diseases or conditions" refers to pathologic conditions that depend on the activity of one or more cathepsins. "Cathepsin K dependent diseases or conditions" refers to pathologic conditions that depend on the activity of Cathepsin K. Diseases associated with Cathepsin K activities include osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, multiple myeloma. Giant cell tumor of the bone represents a further disease that may be associated with Cathepsin K activity. In treating such conditions with compounds of the invention, the required therapeutic amount will vary according to the specific disease and is readily ascertainable by those of skill in the art.

An embodiment of the invention is a method of inhibiting cathepsin activity in a mammal in need thereof, comprising administering to the mammal a therapeutically effective amount of any of the compounds or any of the pharmaceutical compositions described above. The cathepsin activity may be cathepsin K activity.

Another embodiment of the invention is a method of treating or preventing cathepsin dependent conditions in a mammal in need thereof, comprising administering to the mammal a therapeutically effective amount of any of the compounds or any of the pharmaceutical compositions or formulations described herein. The cathepsin activity may be cathepsin K activity.

Another embodiment of the invention is a method of inhibiting bone loss in a mammal in need thereof, comprising administering to the mammal a therapeutically effective amount of any of the compounds or any of the pharmaceutical compositions or formulations described herein. Another embodiment of the invention is a method of reducing bone loss in a mammal in need thereof, comprising administering to the mammal a therapeutically effective amount of any of the compounds or any of the pharmaceutical compositions or formulations described herein. The utility of cathepsin K inhibitors in the inhibition of bone resorption is known. See, for example, Stroup, G. B., Lark, M. W., Veber, D F., Bhattacharrya, A., Blake, S., Dare, L. C., Erhard, K. F., Hoffman, S. J., James, I. E., Marquis, R. w., Ru, Y., Vasko-Moser, J. A., Smith, B. R., Tomaszek, T. and Gowen, M. Potent and selective inhibition of human cathepsin K leads to inhibition of bone resorption in vivo in a nonhuman primate. J. Bone Miner. Res., 16:1739-1746; 2001; and Votta, B. J., Levy, M. A., Badger, A., Dodds, R. A., James, I. E., Thompson, S., Bossard, M. J., Carr, T., Connor, J. R., Tomaszek, T. A., Szewczuk, L., Drake, F. H., Veber, D., and Gowen, M. Peptide aldehyde inhibitors of cathepsin K inhibit bone resorption both in vivo and in vitro. J. Bone Miner. Res. 12:1396-1406; 1997.

Another embodiment of the invention provides a method of treating or preventing osteoporosis in a mammal in need thereof, comprising administering to the mammal a therapeutically effective amount of any of the compounds or any of the pharmaceutical compositions or formulations described herein. The utility of cathepsin K inhibitors in the treatment or prevention of osteoporosis is known; see, for example, Saftig, P., Hunziker, E., Wehmeyer, O., Jones, S., Boyde, A., Rommerskirch, W., Moritz, J. D., Schu, P., and Vonfigura, K. Impaired osteoclast bone resorption leads to osteoporosis in cathepsin K-deficient mice. Proc. Natl. acad. Sci. USA 95:13453-13458; 1998.

Another embodiment of the invention is a method of treating or preventing rheumatoid arthritic condition in a mammal in need thereof, comprising administering to the mammal a therapeutically effective amount of any of the compounds or any of the pharmaceutical compositions or formulations described herein. It is known that progressive destruction of the periarticular bone is a major cause of joint dysfunction and disability in patients with rheumatoid arthritis (RA); see, e.g., Goldring S R, "Pathogenesis of bone erosions in rheumatoid arthritis". Curr. Opin. Rheumatol. 2002; 14: 406-10. Analysis of joint tissues from patients with RA have provided evidence that cathepsin K positive osteoclasts are the cell types that mediate the focal bone resorption associated with rheumatoid synovial lesion (Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74). In addition, generalized bone loss is a major cause of morbidity associated with severe RA. The frequency of hip and spinal fractures is substantially increased in patients with chronic RA (Gould A, Sambrook, P, Devlin J et al, "Osteoclastic activation is the principal mechanism leading to secondary osteoporosis in rheumatoid arthritis". J. Rheumatol. 1998; 25: 1282-9). The utility of cathepsin K inhibitors in the treatment or prevention of resorption in subarticular bone and of generalized bone loss represent a rational approach for pharmacological intervention on the progression of rheumatoid arthritis.

Another embodiment of the invention is a method of treating or preventing the progression of osteoarthritis in a mammal in need thereof, comprising administering to the mammal a therapeutically effective amount of any of the compounds or any of the pharmaceutical compositions or formulations described herein. Osteoarthritis (OA) is accompanied with well-defined changes in the joints, including erosion of the articular cartilage surface, peri-articular endochondral ossificationosteophytosis, and subchondral bony sclerosis and cyst formation (see, e.g., Oettmeier R, Abendroth, K, "Osteoarthritis and bone: osteologic types of osteoarthritis of the hip", Skeletal Radiol. 1989; 18: 165-74). Recently, the potential contribution of subchondral bone sclerosis to the initiation and progression of OA have been suggested. Stiffened subchondral bone as the joint responding to repetitive impulsive loading, is less able to attenuate and distribute forces through the joint, subjecting it to greater mechanical stress across the articular cartilage surface. This in turn accelerates cartilage wear and fibrillate (Radin, E L and Rose R M, "Role of subchondral bone in the initiation and progression of cartilage damage", Clin. Orthop. 1986; 213: 34-40). Inhibition of excessive subarticular bone resorption by an anti-resorptive agent such as a cathepsin K inhibitor, will lead to inhibition of subchondral bone turnover, which may have a favorable impact on OA progression. Cathepsin K protein expression has also been identified in synovial fibroblasts, macrophage-like cells, and chondrocytes from synovium and articular cartilage specimens derived from OA patients (Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74; and Dodd, R A, Connor, J R, Drake, F H, Gowen, M, "Expression of Cathepsin K messenger RNA in giant cells and their precursors in human osteoarthritic synovial tissues". Arthritis Rheumatism 1999; 42: 1588-93; and Konttinen, Y T, Mandelin, J, Li, T-F, Salo, J, Lassus, J et al. "Acidic cysteine endoproteinase cathepsin K in the degeneration of the superficial articular hyaline cartilage in osteoarthritis", Arthritis Rheumatism 2002; 46: 953-60). These studies thus implicated the role of cathepsin K in the destruction of collagen type II in the articular cartilage associated with the progression of osteoarthritis. The utility of cathepsin K inhibitors in the treatment or prevention of osteoarthritis as described in this invention thus comprise of two different mechanisms, one is on the inhibition of osteoclast-driven subchondral bone turnover, and two is on the direct inhibition of collagen type II degeneration in the synovium and cartilage of patients with OA.

Another embodiment of the invention is a method treating cancer in a mammal in need thereof, comprising administering to the mammal a therapeutically effective amount of any of the compounds or any of the pharmaceutical compositions or formulations described herein. It is known that cathepsin K is expressed in human breast carcinoma (Littlewood-Evans A J, Bilbe G, Bowler W B, Farley D, Wlodarski B, Kokubo T, Inaoka T, Sloane J, Evans D B, Gallagher J A, "The osteoclast-associated protease cathepsin K is expressed in human breast carcinoma." Cancer Res 1997 Dec. 1; 57(23):5386-90).

The invention also provides the use of any of the compounds described above in the preparation of a medicament for the treatment and/or prevention of osteoporosis in a mammal in need thereof. Also provided is the use of any of the compounds described above in the preparation of a medicament for the treatment and/or prevention of: bone loss, bone resorption, bone fractures, metastatic bone disease and/or disorders related to cathepsin functioning.

Formulations and Administration

Compounds of the invention may be administered orally, topically, intravenously, subcutaneously, buccally, rectally, dermally, nasally, tracheally, bronchially, by any other parenteral route, as an oral or nasal spray or via inhalation. The compounds may be administered in the form of pharmaceutical preparations comprising prodrug or active compound either as a free compound or, for example, a pharmaceutically acceptable non-toxic organic or inorganic acid or base addition salt, in a pharmaceutically acceptable dosage form. Depending upon the disorder and patient to be treated and the route of administration, the compositions may be administered at varying doses.

Typically, therefore, the pharmaceutical compounds of the invention may be administered orally, topically, or parenterally ("parenterally" as used herein, refers to modes of administration which include intravenous, intramuscular, intraperitoneal, intrasternal, subcutaneous and intraarticular injection and infusion) to a host to obtain a protease-inhibitory effect. In the case of larger animals, such as humans, the compounds may be administered alone or as compositions in combination with pharmaceutically acceptable diluents, excipients or carriers.

Actual dosage levels of active ingredients in the pharmaceutical formulations and pharmaceutical compositions of this invention may be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

In the treatment, prevention, control, amelioration, or reduction of risk of conditions which require inhibition of CatK activity, an appropriate dosage level may generally be about 0.01 to 500 mg per kg patient body weight per day which can be administered in single or multiple doses. The dosage level will be about 0.1 to about 250 mg/kg per day; more preferably about 0.5 to about 100 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0 and 1000.0 milligrams of the active ingredient for the symptomatic adjustment of the dosage to the patient to be treated. The compounds may be administered on a regimen of 1 to 4 times per day, e.g. once or twice per day. The dosage regimen may be adjusted to provide the optimal therapeutic response.

According to a further aspect of the invention there is thus provided a pharmaceutical formulation or composition including a compound of the invention, optionally in admixture with a pharmaceutically acceptable adjuvant, diluents or carrier.

Pharmaceutical formulations or compositions of this invention for parenteral injection may comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservative, wetting agents, emulsifying agents and dispersing agents. Inhibition of the action of microorganisms may be ensured by the inclusion of various antibacterial and antifungal agents, for example, paraben, chlorobutanol or phenol sorbic acid. It may also be desirable to include isotonic agents, such as sugars or sodium chloride, for example. Prolonged absorption of the injectable pharmaceutical form may be brought about by the inclusion of agents (for example, aluminium monostearate and gelatine) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms may be made by forming microencapsule matrices of the drug in biodegradable polymers, for example polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions which are compatible with body tissues. The injectable formulations can be sterilized, for example, by filtration through a bacterial retaining filter or by incorporating sterilizing agents in the form of sterile solid compositions which can be dissolved or dispersed in sterile water or other sterile injectable media just prior to use.

Solid dosage forms for oral administration include capsules, tablets, pills, powders and granules. In such solid dosage forms, the active compound is typically mixed with at least one inert, pharmaceutically acceptable excipient or carrier, such as sodium citrate or dicalcium phosphate and/or one or more: a) fillers or extenders, such as starches, lactose, sucrose, glucose, mannitol and silicic acid; b) binders, such as carboxymethylcellulose, alginates, gelatin, polyvinylpyrrolidone, sucrose and acacia; c) humectants, such as glycerol; d) disintegrating agents, such as agar-agar, calcium carbonate, potato or tapioca starch, alginic acid, certain silicates and sodium carbonate; e) solution retarding agents, such as paraffin; f) absorption accelerators, such as quaternary ammonium compounds; g) wetting agents, such as cetyl alcohol and glycerol monostearate; h) absorbents, such as kaolin and bentonite clay and i) lubricants, such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Oral formulations may contain a dissolution aid. Examples of dissolution aids include nonionic surface active agents, such as sucrose fatty acid esters, glycerol fatty acid esters, sorbitan fatty acid esters (eg sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkyamine oxides; bile acid and salts thereof (eg chenodeoxycholic acid, cholic acid, deoxycholic acid, dehydrocholic acid and salts thereof, and glycine or taurine conjugate thereof); ionic surface active agents, such as sodium laurylsulfate, fatty acid soaps, alkylsufonates, alkylphosphates, ether phosphates, fatty acid salts of basic amino acids; triethanolamine soap, and alkyl quaternary ammonium salts; and amphoteric surface active agents, such as betaines and aminocarboxylic acid salts.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, and/or in delayed fashion. Examples of embedding compositions include polymeric substances and waxes.

The active compounds may also be in microencapsulated form, if appropriate, with one or more of the above-mentioned excipients.

The active compounds may be in finely divided form, for example it may be micronized.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents. Suspensions, in addition to the active compounds, may contain suspending agents such as ethoxylated isostearyl alcohols, polyoxyethylene sorbitol and sorbitan esters, microcrystalline cellulose, aluminium metahydroxide, bentonite, agar-agar, and traganacanth and mixtures thereof.

Compositions for rectal or vaginal administration may be in the form of suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolisable lipid capable of forming liposomes can be used. The present compositions in liposome form can contain, in addition to a compound of the present invention, stabilizers, preservatives, excipients and the like. The preferred lipids are the phospholipids and the phosphatidyl cholines (lecithins), both natural and synthetic. Methods to form liposomes are known in the art, for example, Prescott, Ed., Methods in Cell Biology, Volume XIV, Academic Press, New York, N.Y. (1976), p33 et seq.

Dosage forms for topical administration of a compound of this invention include powders, sprays, creams, foams, gels, ointments and inhalants. The active compound is mixed under sterile conditions with a pharmaceutically acceptable carrier and any needed preservatives, buffers or propellants which may be required. Ophthalmic formulations, eye ointments, powders and solutions are also contemplated as being within the scope of this invention.

Insofar as they do not interfere with the activity of the compounds, the formulations according to the present subject matter may contain other active agents intended, in particular, for use in treating a disease selected from osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy or multiple myeloma. Exemplary other active agents include an organic bisphosphonate, an estrogen receptor modulator, an estrogen receptor beta modulator, an androgen receptor modulator, an inhibitor of osteoclast proton ATPase, an inhibitor of HMG-CoA reductase, an integrin receptor antagonist, or an osteoblast anabolic agent, and the pharmaceutically acceptable salts thereof. Exemplary other active agents are disclosed in US 2014/0256743 A1 at [0623] to [06858], the content of which is hereby incorporated by reference herein.

The formulations according to the present subject matter may also contain inactive components. Suitable inactive components are well known in the art and are described in standard textbooks, such as Goodman and Gillman's: The Pharmacological Bases of Therapeutics, $8^{th}$ Ed., Gilman et al, Eds. Pergamon Press (1990), and Remington's Pharmaceutical Sciences, $17^{th}$ Ed., Mack Publishing Co., Easton, Pa. (1990), both of which are incorporated by reference herein in their entirety.

The formulations may be used in combination with an additional pharmaceutical dosage form to enhance their effectiveness in treating any of the disorders described herein. In this regard, the present formulations may be administered as part of a regimen additionally including any other pharmaceutical and/or pharmaceutical dosage form known in the art as effective for the treatment of any of these disorders.

Assays

Compounds of the invention can be assessed for biological activity using any suitable assay that would be known to the person skilled in the art. Exemplary assays that are useful for the assessment of compounds of the invention are provided in the following paragraphs. In the assays described below, it will be appreciated that the compound to be tested (e.g. a compound of the invention) may be referred to as a "compound" or "inhibitor".

Assay for Indiscriminate Thiol Reactivity

Indiscriminate thiol reactivity may be assessed by quantification of formation of an irreversible cysteine adduct, as is described in R. M. Oballa, J.-F. Truchon, C. I. Bayly, N. Chauret, S. Day, S. Crane, C. Berthelette, *Bioorg. Med. Chem. Lett.* 2007, 17, 998, the content of which is incorporated herein in its entirety. This protocol may be modified to provide a suitable protocol. If a compound forms an adduct with a free thiol in for example cysteine (CAS 52-90-4), this demonstrates indiscriminate thiol reactivity. If a compound does not form an adduct, this indicates that the compound does not show indiscriminate thiol reactivity, e.g. the compound should not show reactivity to cysteine residues in non-targeted proteins.

A specific protocol that may be used is as follows:
Inhibitors were dissolved in DMSO and diluted 100× in aqueous buffer containing 10 mM phosphate pH 7.4 and 10 mM cysteine, to a final concentration of 100 µM inhibitor and 10 mM cysteine. The reaction mixture was incubated at 37° C. for 16 h, after which the sample was injected on the LC-MS. Adduct formation was quantified from peak integration of the UV trace from the peaks corresponding to the remaining compound and the formed adduct, and normalized to 100%.

Indiscriminate thiol reactivity may also be assessed by quantification of formation of an irreversible glutathione (GSH) adduct. A specific protocol that uses GSH is as follows. Inhibitors were dissolved in DMSO and diluted 100× in PBS and 5 mM GSH (ChemImpex Int., 00159), to a final concentration of 100 µM inhibitor and 5 mM GSH. The reaction mixture was incubated at 37° C. for 16 h, after which the sample was injected on the LC-MS. Adduct formation was quantified from peak integration of the UV trace from the peaks corresponding to the remaining compound and the formed adduct, and normalized to 100%.

General Information for In Vitro Activity Assays

Cathepsin (e.g. Cathepsin K/L/V/S/B), in particular purified human Cathepsin, was diluted in freshly prepared reaction buffer consisting of 50 mM MES pH5.5, 25 mM EDTA and 2.5 mM DTT. 0.05% Tween20 (v/v) may be added to the reaction buffer of the Cathepsin K.

Activity assays may be conducted in a suitable manner. In the experiments described herein, the assays were typically conducted in Corning 3820 Low Volume 384 Well Assay Plate with a final assay volume of 20 µL. Plates were shaken at 600 rpm for 1 minute and centrifuged at 1000 rpm for 1 minute prior to incubation. Cathepsin activity was quantified using synthetic fluorogenic peptide substrate Z-FR-AMC (Cath K, L, V), Z-RR-AMC (Cath B) or Z-FVR-AMC (Cath S). Fluorescence intensity ($\lambda_{ex}$=350 nm, $\lambda_{em}$=440 nm) was measured every 2 minutes in arbitrary units (A.U.) on a CLARIOstar (BMG Labtech) microplate reader and values were converted to product formation [AMC]. Dose-response curves were calculated from the initial velocity $v_i$ (slope 0-20 min, steady state kinetics), and fitted to obtain $IC_{50}$-values using non-linear least squares curve fitting (GraphPad Prism 8, inhibitor vs. response—variable slop (four parameters)) with fixed values for the top (DMSO) and bottom (E-64). Measurements were performed in triplicate.

Assay for In Vitro Inhibition of a Cathepsin

Inhibitors (200 nL, 100× final concentration in DMSO) were diluted in reaction buffer (10 µL). Purified human Cathepsin (5 µL, 4× final concentration) was added and the reaction mixture was incubated for 30 min at room temperature. Fluorogenic substrate (5 µL, 4× final concentration) was added and fluorescence intensity was measured every 2 minutes for 30-90 minutes.

This protocol may be adapted for the in vitro analysis of the inhibition of other enzymes (e.g. a non-human Cathepsin) by replacing the human Cathepsin with the enzyme of interest and selecting a suitable fluorogenic substrate of the enzyme of interest.

Assay for Reversibility of Inhibition

Reversibility of protease inhibition by an inhibitor may be assessed in a jump dilution assay. An exemplary jump dilution assay is provided in R. A. Copeland, A. Basavapathruni, M. Moyer, M. P. Scott, *Anal. Biochem.* 2011, 416, 206. In a jump dilution assay the protease (e.g. CatK) is incubated with inhibitor at high concentration to allow full active site occupation, and subsequently diluted, e.g. 300×, into fluorogenic substrate solution resulting in an inhibitor concentration corresponding with full protease activity. The hydrolysis of fluorogenic substrate is monitored over an extended time period, e.g. at least 60 minutes. For a reversible inhibitor, the activity of CatK is regained quickly after dilution, while the activity of CatK remains fully inhibited for irreversible inhibitors. The assay results may be compared with the results using a known irreversible inhibitor of the protease as a control. E-64 represents an established pan-Cathepsin irreversible inhibitor, suitable for use as a positive control with most cysteine protease Cathepsins.

Kinetic Evaluation of Inhibitor Compounds

The reaction kinetics of irreversible covalent inhibitor compounds may be assed in the following manner. Inhibitors (200 nL, 100× final concentration in DMSO) were diluted in reaction buffer (10 µL). Fluorogenic substrate (5 µL, 4× final concentration) was added and the reaction was started by addition of Cathepsin (5 µL, 4× final concentration). Fluorescence intensity was measured every 2 minutes for 60 minutes and fitted to equation I to obtain the $k_{obs}$. The obtained values were plotted against the inhibitor concentration and fitted to equation II to obtain kinetic parameters $k_{inact}$ (rate of covalent bond formation) and $K_I$.

$$[P] = \frac{v_i}{k_{obs}}[1 - e^{-k_{obs}t}] \qquad \text{Equation I}$$

$$k_{obs} = \frac{k_{inact}}{1 + \frac{K_I}{[I]}} \qquad \text{Equation II}$$

LC-MS for Intact CatK and CatK-Inhibitor Complexes.

Cathepsin K (3 µM) in reaction buffer (20 µL) was incubated with inhibitor (100 µM) at 37° C. for 6 hours prior to analysis. 1 µL injections of the sample were made onto a XEVO-G2XSQTOF #YEA928 UPLC-MS system with a Waters Acquity CM detector. Chromatographic separation was carried out on a ACQUITY UPLC® Protein BEH C4 Column over a 12 minute gradient elution of 2% to 100% acetonitrile in water (0.1% formic acid) at a flow rate of 0.500 mL/min. For the first 4 minutes the flow was diverted to the waste to avoid contamination of the MS with high concentrations of buffer components. After 4 minutes, the elution flow was ionized with an ESI ionization source and measured on a XEVO-G2XSQTOF. The results were analyzed using MassLynx V4.1. The total mass of the complex was obtained by deconvolution of electrospray ionization mass spectrum envelope (average isotopes) with the MaxEnt1 function.

EXAMPLES

Example 1: Synthesis of Compounds

The following inhibitor compounds were synthesized:

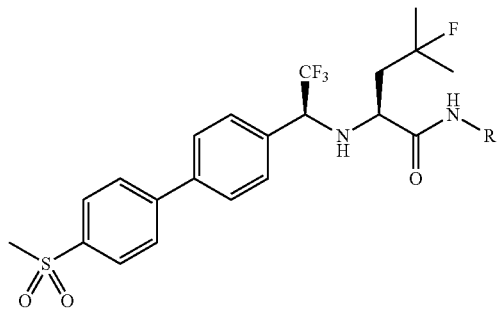

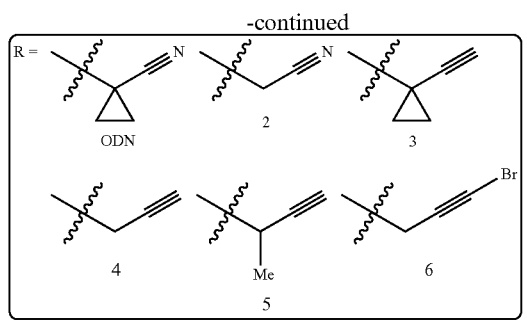

Figure 2:
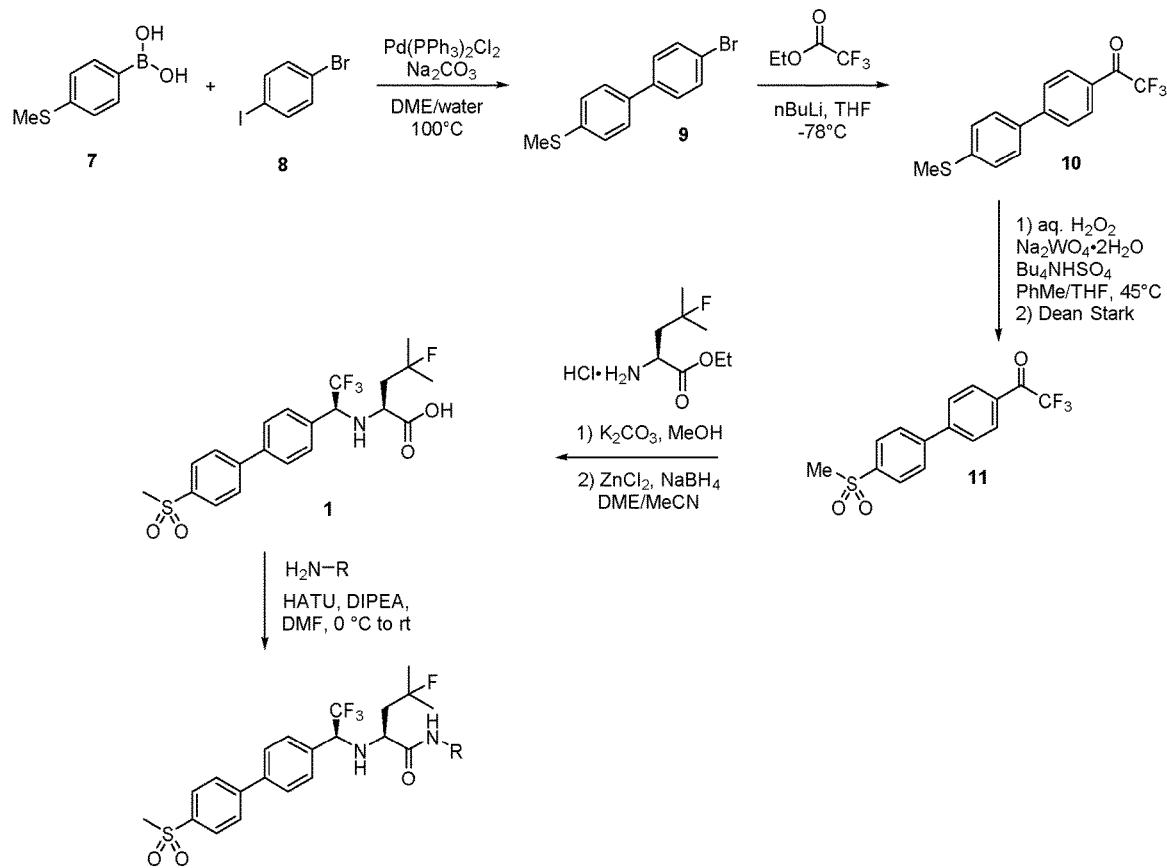
FIG. 2 is a reaction scheme for the synthesis of exemplary alkyne compounds of the invention and reference nitrile compounds.

Synthesis of Odanacatib (ODN) precursors from affordable building blocks has been reported by Sarah Dolman et al (S. J. Dolman, F. Gosselin, P. D. O'Shea, I. W. Davies, *Tetrahedron* 2006, 62, 5092, incorporated by reference herein) and this procedure was altered to obtain ODN-acid 1 (see reaction scheme in FIG. 2).

The electrophilic moieties of the compounds were incorporated using straightforward peptide coupling conditions (see, e.g., P. D. O'Shea, C.-y. Chen, D. Gauvreau, F. Gosselin, G. Hughes, C. Nadeau, R. P. Volante, *The Journal of Organic Chemistry* 2009, 74, 1605) as illustrated in the final reaction step in FIG. 2.

Synthesis of ODN Acid 1

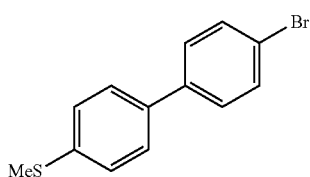 [SMILES: CSc1ccc(-c2ccc(Br)cc2)cc1]

(4'-bromo-[1,1'-biphenyl]-4-yl)(methyl)sulfane 9 (4-(methylthio)phenyl)boronic acid 7 (3.81 gr), 1-bromo-4-iodobenzene 8 (5.83 gr) and sodium carbonate (6.55 gr) were dissolved in a mixture of DME/water (180 mL, 4:1 v/v). The mixture was degassed with argon for 5 minutes, then Bis(triphenylphosphine)palladium(II) dichloride (579 mg) was added and the mixture was heated to 100° C. After stirring for 5 hours, the reaction mixture was allowed to cool to room temperature. The reaction was quenched with water and extracted with EtOAc (2×). The combined organic layers were washed with brine (2×), dried ($Na_2SO_4$) and concentrated under vacuum to give a reddish solid as residue. The crude material was coated on silica and purified by FCC (5% diisopropyl ether in heptane) to give product 9 as a white solid. Spectral data was in agreement with published data (S. J. Dolman, F. Gosselin, P. D. O'Shea, I. W. Davies, Tetrahedron 2006, 62, 5092.)

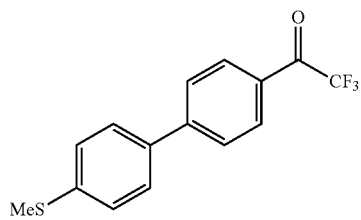 [SMILES: CSc1ccc(-c2ccc(C(=O)C(F)(F)F)cc2)cc1]

2,2,2-trifluoro-1-(4'-(methylthio)-[1,1'-biphenyl]-4-yl)ethanone 10 was obtained according to published procedure ((S. J. Dolman, F. Gosselin, P. D. O'Shea, I. W. Davies, Tetrahedron 2006, 62, 5092.)

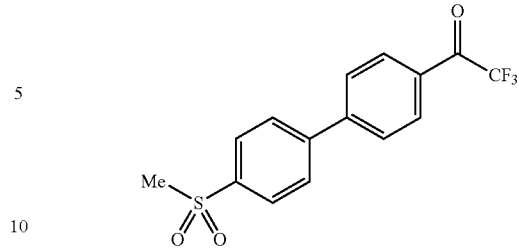

2,2,2-trifluoro-1-(4'-(methylthio)-[1,1'-biphenyl]-4-yl)ethanone 11 was obtained according to published procedure ((S. J. Dolman, F. Gosselin, P. D. O'Shea, I. W. Davies, Tetrahedron 2006, 62, 5092.)

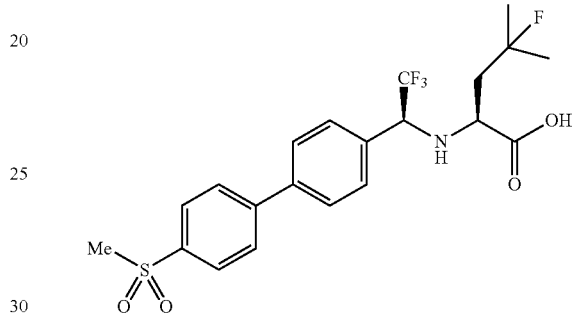

(S)-4-fluoro-4-methyl-2-(((S)-2,2,2-trifluoro-1-(4'-(methylsulfonyl)-[1,1'-biphenyl]-4-yl)ethyl)amino)pentanoic acid 1 was obtained according to published procedure (J. Y. Gauthier, et al., Bioorg. Med. Chem. Lett. 2007, 17, 4929.) Spectral data was in agreement with published data. (J. Y. Gauthier, et al., Bioorg. Med. Chem. Lett. 2008, 18, 923.)

Synthesis of ODN Derivatives

General Procedure A

Odanacatib acid 1 (60 mg) was dissolved in 3 mL DMAc and cooled to 0° C. Amine (1.2 eq.) and HATU (59 mg) were added. The resulting solution was stirred for 15 min and DIPEA (68 mL) was added. The reaction was stirred for 2.5 h. Water was slowly added dropwise and the slurry was stirred 2.5 h at room temperature. The mixture was filtered and the solid material was washed with a 1:1.2 DMF/water solution, water and 2-propanol. The material was removed from the filter by addition of THF. The filtrate was concentrated and purified by FCC (silica, gradient DCM to 2% MeOH in DCM). The products were obtained as a white solid.

General Procedure B

Odanacatib acid 1 (21.3 mg) was dissolved in 700 mL DMF and cooled to 0° C. HATU (21.8 mg) and triethylamine (6 µL) were added. To this solution was added to amine (1.4 eq.) and further triethylamine (12 µL) was added to the mixture. After 2 h ice cooling was removed and the mixture was stirred an additional 2 h. The reaction mixture was concentrated in vacuo, redissolved in EtOAc and extracted with sat. $NH_4Cl$ solution and brine. The organic layer was dried over $Na_2SO_4$ and filtered. The filtrate was concentrated in vacuo and the residue was purified by FCC (silica, gradient DCM to 2% MeOH in DCM), and if needed, further purified using preparative HPLC system and lyophilized to obtain products as a white solid.

(S)—N-(1-cyanocyclopropyl)-4-fluoro-4-methyl-2-(((S)-2,2,2-trifluoro-1-(4'-(methylsulfonyl)-[1,1'-biphenyl]-4-yl)ethyl)amino)pentanamide ODN

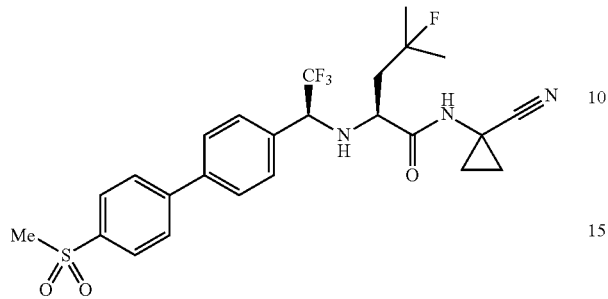

According to general procedure A, the reaction between Odanacatib acid 1 (59.8 mg) and 1-amino-cyclopropanecarbonitrile hydrogenchloride (18.5 mg) afforded product ODN as a white solid 1H NMR (300 MHz, CDCl3) δ=8.03 (d, J=8.4 Hz, 2H), 7.77 (d, J=8.8 Hz, 2H), 7.65 (d, J=8.1 Hz, 2H), 7.48 (d, J=8.1 Hz, 2H), 7.42 (s, 1H), 4.17 (q, J=7.2 Hz, 1H), 3.59 (dd, J=8.9, 3.3 Hz, 1H), 3.10 (s, 3H), 2.17-1.85 (m, 2H), 1.56-1.44 (m, 2H), 1.47 (d, J=21.7 Hz, 3H), 1.44 (d, J=22.0 Hz, 3H), 1.11-0.85 (m, 2H). 13C NMR (75 MHz, CDCl3) δ=174.42, 145.69, 140.57, 139.94, 134.53, 129.40, 128.22, 128.20, 126.02 (q, J=279.3 Hz), 119.56, 96.84 (d, J=163.8 Hz), 63.44 (q, J=29.3 Hz), 59.03, 44.75, 43.64 (d, J=19.9 Hz), 28.37 (d, J=24.4 Hz), 25.83 (d, J=24.7 Hz), 20.21, 16.86, 16.48. HRMS (ESI+): calculated for C25H28F4N3O3S [M+H]+ 526.1788, found: 526.1816.

(S)—N-(cyanomethyl)-4-fluoro-4-methyl-2-(((S)-2,2,2-trifluoro-1-(4'-(methylsulfonyl)-[1,1'-biphenyl]-4-yl)ethyl)amino)pentanamide 2

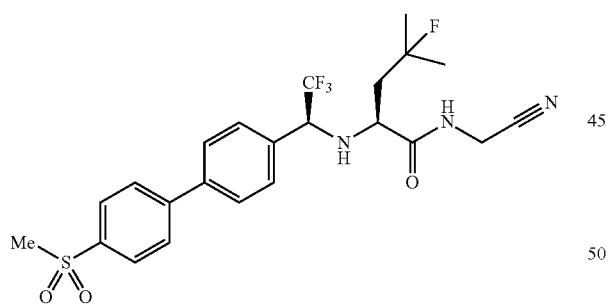

According to general procedure B, the reaction between Odanacatib acid 1 (21.8 mg) and aminoacetonitrile (6.2 mg) afforded product 2 as a white solid 1H NMR (300 MHz, CDCl3) δ=8.01 (d, J=8.4 Hz, 2H), 7.76 (d, J=8.4 Hz, 2H), 7.65 (d, J=8.4 Hz, 2H), 7.50 (d, J=8.2 Hz, 2H), 7.45 (t, J=6.7 Hz, 1H), 4.24 (q, J=7.1 Hz, 1H), 4.21-3.96 (m, 2H), 3.66 (dd, J=8.8, 3.3 Hz, 1H), 3.10 (s, 3H), 2.21-1.89 (m, 2H), 1.47 (d, J=21.7 Hz, 3H), 1.45 (d, J=22.0 Hz, 3H). 13C NMR (75 MHz, CDCl3) δ=173.80, 145.74, 140.46, 139.70, 134.18, 129.40, 128.21, 128.15, 125.40 (q, J=282.9 Hz), 115.67, 96.84 (d, J=163.7 Hz), 63.12 (q, J=28.7 Hz), 58.45, 44.73, 43.58 (d, J=19.9 Hz), 28.41 (d, J=24.2 Hz), 27.33, 25.72 (d, J=24.7 Hz). HRMS (ESI+): calculated for C23H26F4N3O3S [M+H]+ 500.1631, found: 500.1638.

(S)—N-(1-ethynylcyclopropyl)-4-fluoro-4-methyl-2-(((S)-2,2,2-trifluoro-1-(4'-(methylsulfonyl)-[1,1'-biphenyl]-4-yl)ethyl)amino)pentanamide 3

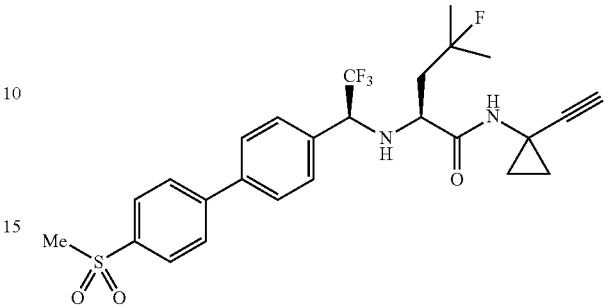

According to general procedure A, the reaction between Odanacatib acid 1 (60.7 mg) and 1-ethynylcyclopropane-1-amine hydrochloric acid 16 (18.3 mg) afforded product 3 as a white solid 1H NMR (300 MHz, CDCl3) δ=8.02 (d, J=8.5 Hz, 2H), 7.76 (d, J=8.4 Hz, 2H), 7.62 (d, J=8.3 Hz, 2H), 7.47 (d, J=8.1 Hz, 2H), 7.32 (s, 1H), 4.14 (q, J=7.2 Hz, 1H), 3.58 (dd, J=9.0, 3.2 Hz, 1H), 3.10 (s, 3H), 2.94 (s, 1H), 2.10 (s, 1H), 2.19-1.84 (m, 2H), 1.46 (d, J=21.7 Hz, 6H), 1.43 (d, J=22.0 Hz, 6H), 1.27-1.07 (m, 2H), 0.95-0.86 (m, 1H), 0.75-0.66 (m, 1H). 13C NMR (75 MHz, CDCl3) δ=173.85, 145.80, 140.20, 139.71, 134.96, 129.34, 128.15, 127.96, 125.50 (q, J=283.1 Hz), 97.00 (d, J=163.3 Hz), 84.69, 66.97, 63.04 (q, J=28.8 Hz), 59.15, 44.71, 43.57 (d, J=19.9 Hz), 27.22 (d, J=200.7 Hz), 26.90 (d, J=201.0 Hz), 22.48, 17.72, 17.20. HRMS (ESI+): calculated for C26H29F4N2O3S [M+H]+ 525.1835, found: 525.1824.

(S)-4-fluoro-4-methyl-N-(prop-2-yn-1-yl)-2-(((S)-2,2,2-trifluoro-1-(4'-(methylsulfonyl)-[1,1'-biphenyl]-4-yl)ethyl)amino)pentanamide 4

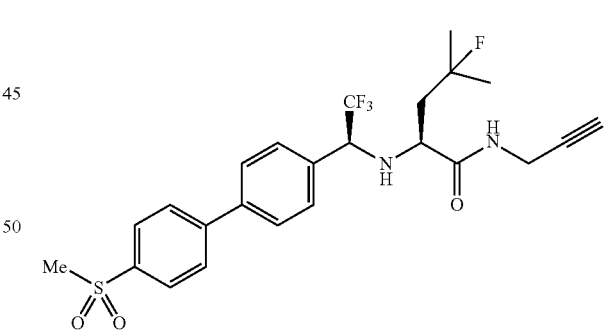

According to general procedure B, the reaction between Odanacatib acid 1 (20.6 mg) and propargylamine (10 μL) afforded product 4 as a white solid 1H NMR (300 MHz, CDCl3) δ=8.02 (d, J=8.5 Hz, 2H), 7.76 (d, J=8.6 Hz, 2H), 7.63 (d, J=8.4 Hz, 2H), 7.51 (d, J=8.1 Hz, 2H), 7.22 (t, J=5.5 Hz, 1H), 4.23 (q, J=7.2 Hz, 1H), 3.94 (qdd, J=17.6, 5.5, 2.6 Hz, 2H), 3.69 (dd, J=9.2, 3.1 Hz, 1H), 3.42 (s, 1H), 3.10 (s, 3H), 2.18 (t, J=2.6 Hz, 1H), 2.14-1.89 (m, 2H), 1.48 (d, J=21.7 Hz, 3H), 1.45 (d, J=22.0 Hz, 3H). 13C NMR (75 MHz, CDCl3) δ=173.80, 145.87, 140.25, 139.68, 134.60, 129.43, 128.17, 128.02, 125.54 (q, J=283.3 Hz), 97.01 (d, J=163.5 Hz), 78.91, 71.89, 62.98 (q, J=28.7 Hz), 58.72, 44.74, 43.73 (d, J=19.8 Hz), 29.19, 28.55 (d, J=24.5 Hz), 25.49 (d, J=24.8 Hz). HRMS (ESI+): calculated for C24H27F4N2O3S [M+H]+ 499.1679, found: 499.1713.

(S)—N—((R/S)-but-3-yn-2-yl)-4-fluoro-4-methyl-2-(((S)-2,2,2-trifluoro-1-(4'-(methylsulfonyl)-[1,1'-biphenyl]-4-yl)ethyl)amino)pentanamide 5

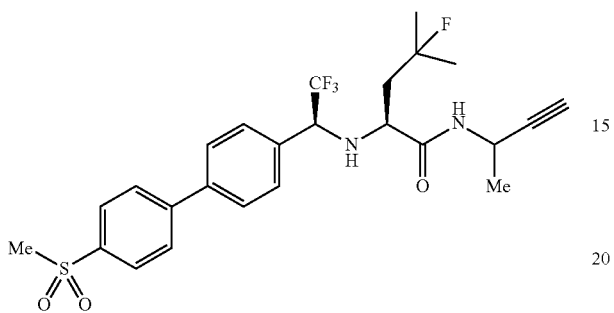

According to general procedure B, the reaction between Odanacatib acid 1 (19.9 mg) and 1-methyl-prop-2-ynylamine hydrochloride (16.5 mg) afforded an inseparable 1:1 mixture of diastereoisomers (S,S,R)-5 and (S,S,S)-5 as a white solid Reported ppm-values are average values. 1H NMR (300 MHz, CDCl3) δ=8.02 (d, J=8.6 Hz, 2H), 7.76 (d, J=8.6 Hz, 2H), 7.63 (d, J=8.3 Hz, 2H), 7.51 (d, J=8.2 Hz, 2H), 7.21 (d, J=8.3 Hz, 1H), 4.74-4.58 (m, 1H), 4.20 (q, J=14.5 Hz, 1H), 3.68 (t, J=7.7 Hz, 1H), 3.60 (s, 1H), 3.10 (s, 3H), 2.20 (d, J=9.0 Hz, 1H), 2.16-1.86 (m, 2H), 1.47 (dd, J=22.0, 10.0 Hz, 6H), 1.24 (d, J=6.9 Hz, 3H). 13C NMR (75 MHz, CDCl3) δ=173.04, 145.86, 140.24, 139.69, 134.82, 129.42, 128.09, 125.54 (q, J=283.6 Hz), 97.06 (d, J=163.4 Hz), 83.44, 70.75, 63.03 (q, J=28.6 Hz), 59.03, 44.74, 43.71 (d, J=19.8 Hz), 36.92, 28.62 (d, J=24.3 Hz), 25.37 (d, J=24.7 Hz), 21.95. HRMS (ESI+): calculated for C25H29F4N2O3S [M+H]+ 513.1835, found: 513.1829.

(S)—N-(3-bromoprop-2-yn-1-yl)-4-fluoro-4-methyl-2-(((S)-2,2,2-trifluoro-1-(4'-(methylsulfonyl)-[1,1'-biphenyl]-4-yl)ethyl)amino)pentanamide 6

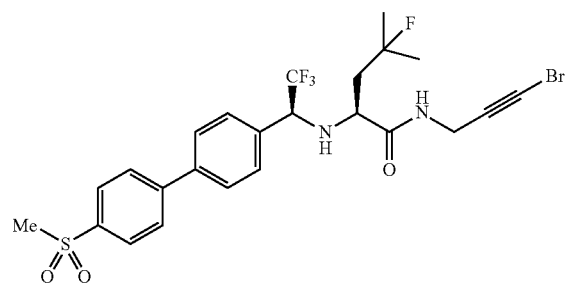 [SMILES: CC(C)(F)C[C@H](N[C@@H](c1ccc(-c2ccc(S(C)(=O)=O)cc2)cc1)C(F)(F)F)C(=O)NCC#CBr]

According to general procedure A, the reaction between Odanacatib acid 1 (60.8 mg) and 3-bromoprop-2-yn-1-amine hydrochloric acid 19 (26.6 mg) afforded product 6 as a white solid 1H NMR (300 MHz, CDCl3) δ=8.03 (d, J=8.4 Hz, 2H), 7.78 (d, J=8.4 Hz, 2H), 7.65 (d, J=8.2 Hz, 2H), 7.50 (d, J=8.1 Hz, 2H), 7.16 (t, J=5.3 Hz, 1H), 4.21 (q, J=7.2 Hz, 1H), 4.13-3.81 (m, 2H), 3.68 (dd, J=9.2, 3.1 Hz, 1H), 3.11 (s, 3H), 2.20-1.88 (m, 3H), 1.49 (d, J=21.7 Hz, 6H), 1.45 (d, J=22.0 Hz, 6H). 13C NMR (75 MHz, CDCl3) δ=173.11, 145.89, 140.18, 139.66, 134.75, 129.38, 128.18, 128.14, 128.00, 125.60 (q, J=283.5 Hz), 97.01 (d, J=163.4 Hz), 75.53, 62.92 (q, J=28.6 Hz), 58.94, 44.73, 43.80 (d, J=19.9 Hz), 43.21, 30.00, 28.57 (d, J=24.4 Hz), 25.51 (d, J=24.7 Hz). HRMS (ESI+): calculated for C24H26BrF4N2O3S [M+H]+ 577.0784, found: 577.0809 (minor)

Synthesis of Alkyne 16

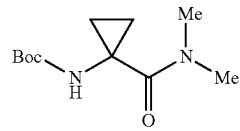 [SMILES: CN(C)C(=O)C1(NC(=O)OC(C)(C)C)CC1]

tert-butyl(1-(methoxy(methyl)carbamoyl)cyclopropyl)carbamate 13

A solution of 1-(Boc-amino)cyclopropanecarboxylic acid (200 mg) in DCM (2.5 mL) under argon was cooled to −15° C. N,O-Dimethylhydroxylamine hydrochloride (1.02 mmol) was added, followed by 4-methylmorpholine (113 mL). After 5 min, 1-(3-methylaminopropyl-3-ethylcarbodiimide hydrochloride (194.5 mg) was added and the reaction was allowed to reach room temperature and stirred overnight. Water was added and the solution was extracted with DCM (3×). The combined organic phases were washed with brine, dried (Na2SO4), and concentrated in vacuo to obtain pure Weinreb amide 13 as an off white solid. 1H NMR (300 MHz, CDCl3) δ 5.22 (s, 1H), 3.74 (s, 3H), 3.18 (s, 3H), 1.44 (q, J=5.2 Hz, 2H), 1.44 (s, 9H), 1.03 (q, J=4.8 Hz, 2H). 13C NMR (75 MHz, DMSO-d6) δ=171.87, 155.31, 78.00, 60.64, 34.00, 28.15, 21.16, 14.69.

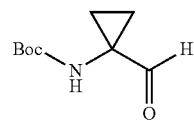

tert-butyl (1-formylcyclopropyl)carbamate 14

Tert-butyl (1-(methoxy(methyl)carbamoyl)cyclopropyl)carbamate 13 (500 mg) was dissolved in anhydrous Et2O (50 mL) under argon and cooled to 0° C. Lithium Aluminum Hydride (3 mL, 1 M in Et2O) was added dropwise and the reaction mixture was stirred for 2 h at this temperature. The reaction was quenched by addition of 1N HCl (2.5 mL) and stirred vigorously for a few minutes. The organic layer was extracted with 1N HCl and brine, dried over Na2SO4, filtered and concentrated to obtain the product aldehyde 14 as a colorless oil. Use crude in the next step.

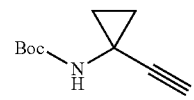

tert-butyl (1-ethynylcyclopropyl)carbamate 15

Dimethyl (1-diazo-2-oxopropyl)phosphonate (443 mL) was dissolved in MeCN (25 mL) and potassium carbonate (767 mg) was added. The suspension was stirred at room temperature for 10 minutes, then the freshly prepared aldehyde 14 (428 mg) in MeOH (9 mL) was added. Stirring was continued overnight. The solvents were removed in vacuo and the residue was dissolved in 1:1 mixture of Et$_2$O/water. The layers were separated and the organic layer was washed with water and brine, and dried (Na$_2$SO$_4$). The yellowish oil was purified by FCC (1:2 EtOAc/heptane) to give product 15 as a pale white solid. $^1$H NMR (300 MHz, CDCl$_3$) δ=5.00 (s, 1H), 2.13 (s, 1H), 1.46 (s, 9H), 1.23-1.16 (m, 2H), 1.12-1.01 (m, 2H). $^{13}$C NMR (75 MHz, CDCl$_3$) δ=155.47, 85.80, 80.34, 66.75, 28.49, 23.72, 18.13.

1-ethynylcyclopropane-1-amine hydrochloric Acid 16

To a solution of tert-butyl (3-bromoprop-2-yn-1-yl)carbamate 15 (165 mg) in MeOH (4.5 mL) was added 1.25 M HCl in MeOH (1.82 mL). The reaction mixture was left to stir overnight, volatiles were removed in vacuo and the resulting solid was triturated with Et$_2$O to obtain alkyne 16 as a white solid. $^1$H NMR (300 MHz, DMSO-d$_6$) δ 8.74 (s, 3H), 3.59 (s, 1H), 1.26 (m, 2H), 1.23-1.07 (m, 2H). $^{13}$C NMR (75 MHz, DMSO-d$_6$) δ=81.75, 74.40, 23.86, 13.72.

Synthesis of Alkyne 19

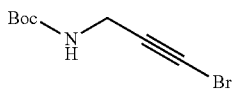

tert-butyl (3-bromoprop-2-yn-1-yl)carbamate 18

Tert-butyl prop-2-yn-1-ylcarbamate (583.4 mg) was dissolved in 19 mL DMF and silver nitrate (64 mg) was added, followed by the addition of N-bromosuccinimide (735 mg). The mixture was covered with aluminum foil and stirred at room temperature for 2 h, and was diluted with EtOAc and extracted with water (2×). The combined organic layers were dried over Na$_2$SO$_4$, filtered over celite and concentrated to give a yellow solid. The crude material was purified by FCC (3:1 to 2:1 EtOAc in hept) to give bromoalkyne 18 as an off white solid. $^1$H NMR (300 MHz, CDCl$_3$) δ=4.69 (s, 1H), 3.94 (d, J=5.5 Hz, 2H), 1.45 (s, 9H). $^{13}$C NMR (75 MHz, CDCl$_3$) δ=155.31, 80.22, 76.46, 42.75, 31.51, 28.43.

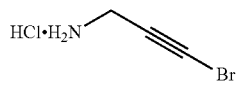

3-bromoprop-2-yn-1-amine hydrochloric Acid 19

To tert-butyl (3-bromoprop-2-yn-1-yl)carbamate 18 (0.29 mmol) was added 4 M HCl in dioxane (8 mmol). The reaction mixture was left to stir 1 h, volatiles were removed in vacuo and the resulting solid was triturated with Et$_2$O to obtain product 19 as a white solid. $^1$H NMR (300 MHz, DMSO-d$_6$) δ=8.58 (s, 3H), 3.75 (s, 2H). $^{13}$C NMR (75 MHz, CDCl$_3$) δ=73.49, 48.94, 29.24.

Example 2: Assessment of Indiscriminate Thiol Reactivity

The compounds assessed and results obtained in the indiscriminate thiol reactivity assay with cysteine are summarized in Table 1. The compounds Ibrutinib, 4, 5 and 6 were also assessed in the indiscriminate thiol reactivity assay with GSH, where Ibrutinib formed 74% adduct, each of 4 and 5 formed 0% adduct, and 6 formed 54% adduct.

TABLE 1

| Indiscriminate thiol reactivity | |
|---|---|
| Compound | Adduct |
| ODN | 25% |
| 2 | 79% |
| 3 | 0% |
| 4 | 0% |
| 5 | 0% |
| 6 | 50% |
| E-64 | 32% |
| Ibrutinib | 97% |
| Afatinib | 99% |

ODN and nitrile compound 2 show significant adduct formation, as do acrylamide-based inhibitors Ibrutinib (Gleevac) and Afatinib (Iressa), and established irreversible Cathepsin inhibitor E-64 (Sigma Aldrich, CAS 66701-25-5). Adduct formation was not detected for alkyne-based inhibitors 3, 4 and 5. This supports our hypothesis that, in compounds of the invention (in particular compounds of the invention that do not comprise a halide directly attached to the alkyne), the alkyne is not reactive towards cysteine residues in non-targeted proteins.

Example 3: Inhibition of Human Cathepsin—Recombinant Material

The potency of the compounds as CatK inhibitors was assessed in an in vitro inhibition assay on purified human CatK (Table 2). Cathepsin was incubated with inhibitor, and the hydrolysis of substrate was initiated by addition of substrate. Alkyne-based inhibitors are less potent than nitrile-based ODN, but selectivity for CatK over structurally related human Cathepsins was conserved for alkynes 4 and 5, while all selectivity is lost for bromoalkyne 6.

TABLE 2 in vitro IC$_{50}$ values (nM) against proteolytic activity of various purified human Cathepsins[*]

| Compound | hCatK | hCatL | hCatS | hCatV | hCatB |
|---|---|---|---|---|---|
| ODN | 0.56 ± 0.002 | 5353 ± 596 | 24.3 ± 0.569 | 605 ± 40.1 | 62.6 ± 2.50 |
| 2 | 0.57 ± 0.009 | >1000 | 17.8 ± 0.303 | 909 ± 105 | 20.9 ± 0.657 |
| 3 | 26160 ± 2238 | >100000 | >100000 | >100000 | >100000 |
| 4 | 293 ± 8.73 | >100000 | 10690 ± 842 | 23800 ± 1409 | 9387 ± 628 |
| 5 | 346 ± 11.6 | >100000 | 15930 ± 1838 | 45900 ± 2333 | 39700 ± 4342 |
| 6 | 46.9 ± 1.81 | 102.5 ± 5.14 | 55.4 ± 2.94 | 16.2 ± 0.883 | 98.6 ± 5.88 |
| E-64 | 1.9 ± 0.032 | 3.5 ± 0.220 | | | |

[c] Mean ± SD for a single representative experiment (triplicate measurement)

Figure 3:
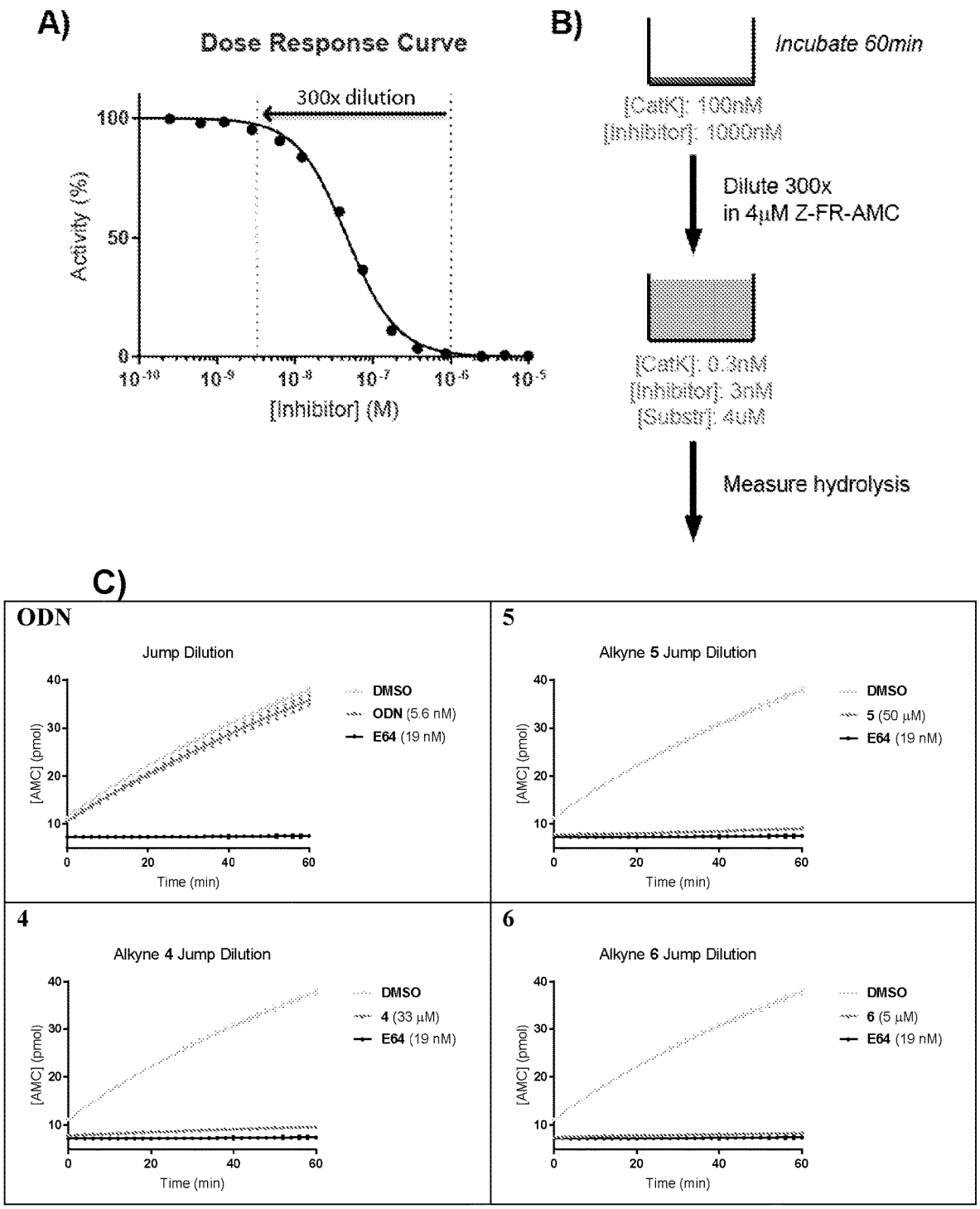
FIG. 3 provides a schematic overview of a jump dilution assay. A) Dose response curve for a 300-fold dilution of inhibitor concentration from full inhibition to full activity. B) Protocol and concentrations for incubation and dilution. C) Progress curves for hCatK proteolytic activity with inhibitor compounds ODN, 4, 5, 6 after dilution.

Reversibility of hCatK inhibition was assessed in a jump dilution assay. Established pan-Cathepsin inhibitor E-64 was taken along as a control for irreversible inhibition. Purified hCatK was incubated with inhibitors at high concentration to allow full active site occupation, and subsequently diluted 300× into fluorogenic substrate solution resulting in an inhibitor concentration corresponding with full activity (FIG. 3). From the obtained results it was concluded that ODN is a (fast) reversible inhibitor, while inhibition by alkynes 4, 5 and 6 is irreversible.

Figure 4:
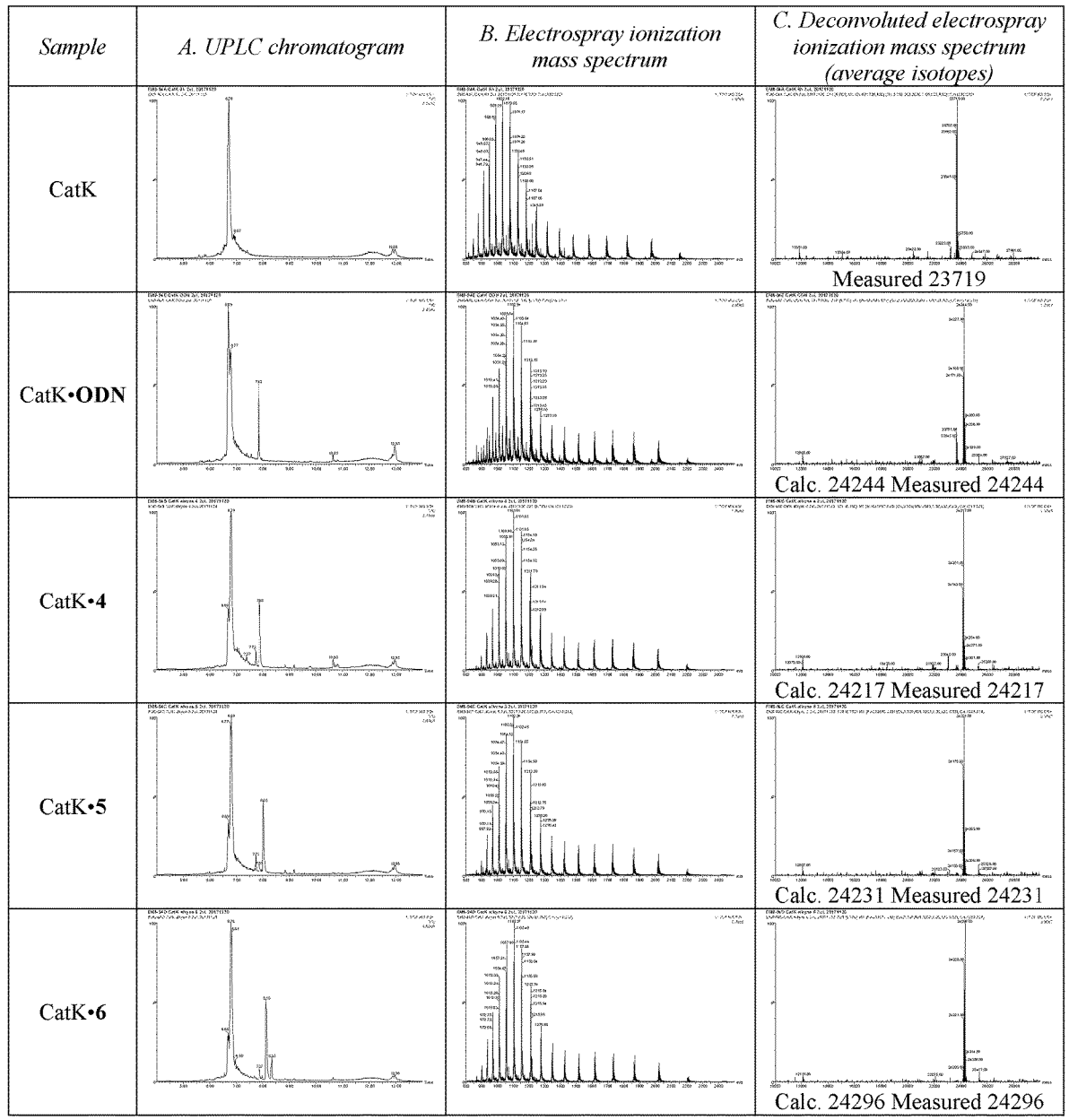
FIG. 4 provides representative mass measurements obtained from LC/MS data of intact covalent complex formed on incubation of human CatK with an inhibitor for 6 h at 37° C. The masses were determined from deconvoluted electrospray ionization mass spectra of CatK complexes.

Cathepsin K was incubated with ODN, 4, 5 or 6 for 6 h to allow full covalent bond formation and submitted for measurement without any digestion steps, according to the method for LC-MS for intact CatK and CatK-inhibitor complexes described in the assays section above. The results are shown in FIG. 4 and summarised in Table 3. LC-MS measurement of intact CatK and intact CatK-inhibitor complexes clearly showed an increase in the deconvoluted mass, corresponding to addition of the inhibitor to hCatK for inhibitors 4, 5 and 6, confirming the formation of a covalent hCatK-inhibitor complex.

TABLE 3

LC-MS evaluation of intact protein CatK-inhibitor complexes

| Compound | MW Inhibitor | Calculated mass complex | Measured mass complex |
|---|---|---|---|
| CatK | — | — | 23719 |
| CatK•ODN | 525 g/mol | 24244 | 24244 |
| CatK•4 | 498 g/mol | 24217 | 24217 |
| CatK•5 | 512 g/mol | 24231 | 24231 |
| CatK•6 | 577 g/mol | 24296 | 24296 |

Kinetic evaluation of irreversible covalent inhibitors was conducted by following the progress curve of inhibition when the hydrolysis of substrate is started by addition of the enzyme (instead of incubating the protease with the inhibitor prior to addition of the substrate). From this curve the maximum rate of covalent bond formation ($k_{inact}$) could be determined (Table 4). The maximum rate of covalent bond formation ($k_{inact}$) did not correlate with indiscriminate thiol reactivity of the alkyne, as $k_{inact}$ for alkyne 4 and 5 is faster than for bromoalkyne 6, even though bromoalkyne 6 is more electrophilic.

TABLE 4

In vitro kinetic evaluation of covalent (ir)reversible inhibitors on purified hCatK

| | $K_{inact}$ (min$^{-1}$) | $K_I$ (nM) | $K_{inact}/K_I$ (M$^{-1}$min$^{-1}$) |
|---|---|---|---|
| 4 | 0.011 | 212 | 53 × 10$^3$ |
| 5 | 0.047 | 3253 | 15 × 10$^3$ |
| 6 | 0.019 | 193 | 99 × 10$^3$ |
| E-64 | 0.081 | 11.4 | 70 × 10$^5$ |

[*] 100 pM hCatK, 4 μM fluorogenic substrate Z-FR-AMC, 26° C. Reaction initialization by addition of CatK.

Example 4: Inhibition of Bone Resorption in Human Osteoclasts'

Figure 5:
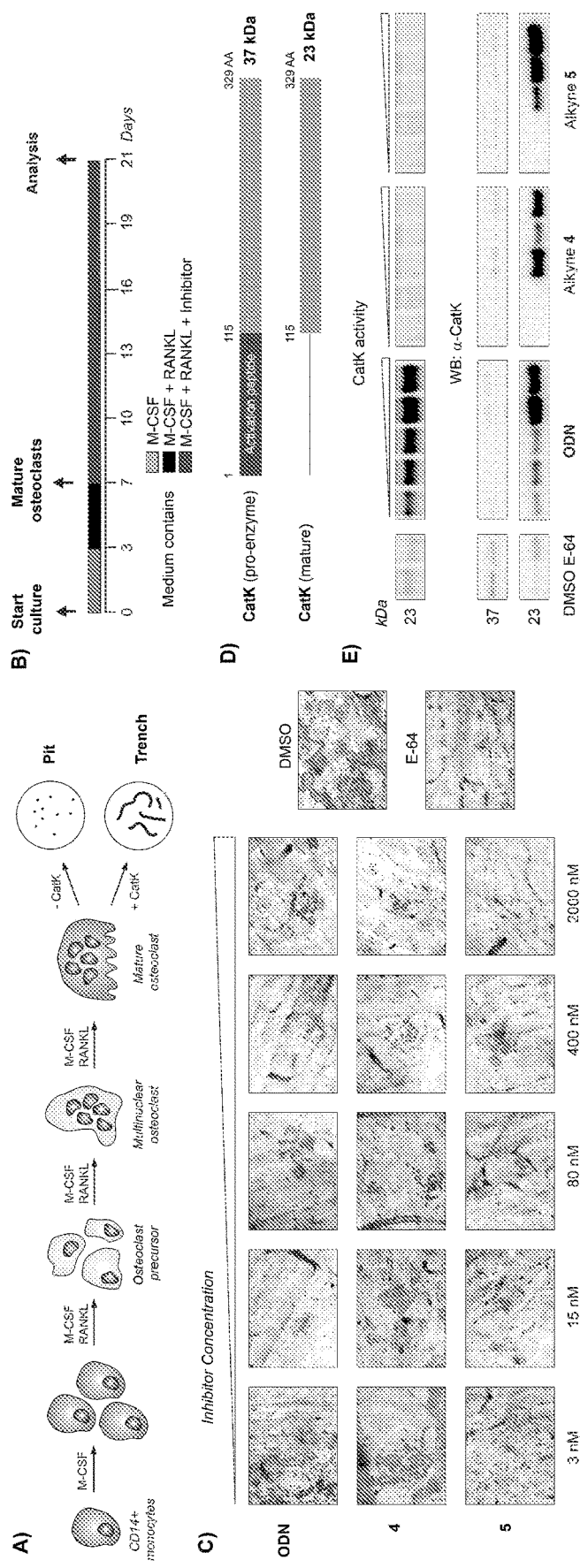
FIG. 5 shows the inhibition of osteoclastic CatK when human osteoclasts (OCs) are cultured on cortical bone slices with an inhibitor of this invention.

The inhibitory properties on CatK of inhibitors of this invention were tested in a biologically relevant setting: inhibition of bone resorption by osteoclasts (OCs). OCs are the cells that degrade the bone matrix by secretion of acid and CatK into the resorption lacunae, resulting in the cleavage of collagen type I. Inhibition of osteoclastic CatK was studied by culturing OCs on cortical bone slices in presence of inhibitors of this invention (FIG. 5). FIG. 5 shows CatK inhibition in human osteoclasts (OCs) by inhibitors of this invention: A) Maturation of OCs from monocytes. OCs predominantly form deep trenches (paths) while OCs lacking CatK form small pits (circular dots). B) CD14+ monocytes on bone slices were treated with MCSF (day 0) and RANKL (day 3) to stimulate differentiation to mature OCs. Medium containing either an inhibitor or DMSO was refreshed on day 7, 10, 13 and 16. At day 21, OCs were washed away and lysed, and bone slices were stained to visualize bone resorption. C) Bone resorption visualized by staining of resorption pits with Coomassie Brilliant Blue. More staining means more resorption pits, thus more bone resorption activity. Normal D) Schematic overview of pro-Cathepsin K activation. E) CatK activity and expression in OC lysates. Top: fluorescence scan of CatK bound to activity-based probe BMV109 shows active CatK. Bottom: Western Blotting against CatK shows total amount of CatK present in lysate. Darker bands indicate more activity/expression of CatK.

Staining of bone slices for bone resorption showed formation of deep trenches for samples treated with 3 nM ODN, while 15 nM ODN resulted in the formation of shallow pits (FIG. 5C), corresponding to an effective dose of around 15 nM. Treatment with inhibitor 4 successfully inhibited bone resorption at concentrations from 80 nM, while inhibition with inhibitor 5 was non-conclusive; trenches as well as pits were observed at all tested concentrations.

OC lysates were treated with activity-based irreversible Cathepsin probe BMV109 to assess whether the observed inhibition of bone resorption could be correlated with CatK activity (FIG. 5E). Samples treated with high concentrations of 4 and 5 showed full inhibition of CatK activity, while a strong increase of mature CatK activity was observed in all samples treated with ODN, because of displacement of the reversible inhibitor with the irreversible probe. Western blotting for CatK revealed an increase in the levels of mature CatK inside the OCs that were treated with high concentrations of inhibitor, confirming that mature CatK is present in the OCs treated with inhibitor 4 or 5, but that its catalytic activity has been inhibited.

The invention claimed is:

1. A compound of formula I:

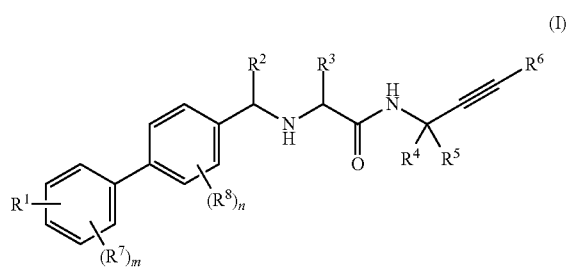

(I)

wherein:
$R^1$ is —S(O)$_2$R$^a$, —C(O)R$^a$, —H, —X, —CN, —C$_1$-C$_6$ substituted or unsubstituted alkyl, C$_3$-C$_6$ substituted or unsubstituted cycloalkyl, —C$_1$-C$_6$ alkoxy, —C$_3$-C$_6$ cycloalkoxy, —NHC(O)R$^a$, —NHC(O)NHR$^a$, —C$_2$-C$_5$ lactam, or —C$_1$-C$_4$ cyclourea; and R$^1$ is located para or meta to the phenylene moiety;
$R^2$ is —C$_1$-C$_4$ alkyl, —C$_1$-C$_4$ haloalkyl, or =O;
$R^3$ is —C$_2$-C$_6$ alkyl, or —C$_2$-C$_6$ haloalkyl;
$R^4$ and $R^5$ are independently selected from —H, —C$_1$-C$_3$ alkyl, or —C$_1$-C$_3$ haloalkyl, or R$^4$ and R$^5$ together with the carbon atom to which they are attached form a C$_3$-C$_6$ cycloalkyl, C$_3$-C$_6$ heterocycloalkyl, or C$_3$-C$_6$ cyclohaloalkyl;
$R^6$ is —H, —Y, —CH$_3$, —CY$_3$, —CHY$_2$, —CH$_2$Y;
each $R^7$ is independently selected from —H, —X, —CN, —C$_1$-C$_4$ alkyl, —C$_1$-C$_4$ haloalkyl, or —C$_1$-C$_3$ alkoxy;
each $R^8$ is independently selected from —X, —C$_1$-C$_4$ alkyl, or —C$_1$-C$_4$ haloalkyl;
$R^a$ is —H, —C$_1$-C$_6$ substituted or unsubstituted alkyl, —NH$_2$, or —NR$^9$R$^{10}$;
each X is independently selected from —F, —Cl, —Br, or —I;
$R^9$ and $R^{10}$ are independently selected from —H, —C$_1$-C$_3$ alkyl, or —C$_1$-C$_3$ haloalkyl; or R$^9$ and R$^{10}$ together with the nitrogen atom to which they are attached to form a C$_3$-C$_6$ heterocycloalkyl;
Y is —F, —Cl, —Br, or —I;
m is 0, 1, 2, 3, or 4; and
n is 0, 1 or 2,
or a pharmaceutically acceptable salt or stereoisomer thereof.

2. The compound of claim 1, wherein R$^1$ is —S(O)$_2$R$^a$ or —CH$_3$.

3. The compound of claim 1, wherein R$^a$ is —C$_1$-C$_4$ alkyl.

4. The compound of claim 1, wherein R$^1$ is located para to the phenylene moiety.

5. The compound of claim 1, wherein R$^2$ is —C$_1$-C$_4$ haloalkyl, —C$_1$-C$_2$ haloalkyl, or —CF$_3$.

6. The compound of claim 5, wherein the haloalkyl in R$^2$ is fluoroalkyl.

7. The compound of claim 1, wherein R$^3$ is —C$_2$-C$_6$ haloalkyl, —C$_4$ haloalkyl, or —CH$_2$C(CH$_3$)$_2$F.

8. The compound of claim 7, wherein the haloalkyl in R$^3$ is fluoroalkyl.

9. The compound of claim 1, wherein R$^4$ and/or R$^5$ is —H, —CH$_3$, or —CH$_2$CH$_3$.

10. The compound of claim 1, wherein R$^4$ and R$^5$ together with the carbon atom to which they are attached form a C$_3$-C$_6$ cycloalkyl.

11. The compound of claim 10, wherein R$^4$ and R$^5$ together with the carbon atom to which they are attached form a C$_3$ cycloalkyl.

12. The compound of claim 1, wherein R$^6$ is —H, —CH$_3$, —CY$_3$, —CHY$_2$, or —CH$_2$Y.

13. The compound of claim 1, wherein R$^7$ and/or R$^8$ is —X or —C$_1$-C$_4$ alkyl.

14. The compound of claim 1, wherein m is 0 and/or n is 0.

15. The compound of claim 1, wherein the compound is a compound of formula IIIa:

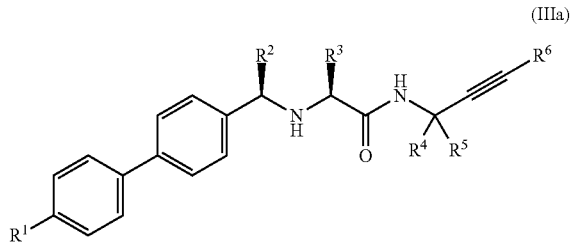

(IIIa)

or a pharmaceutically acceptable salt thereof.

16. The compound of claim 1, selected from:

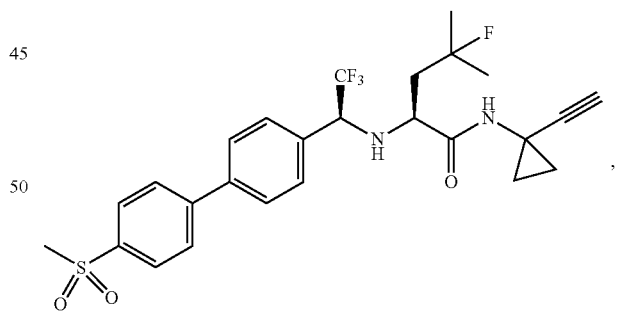

,

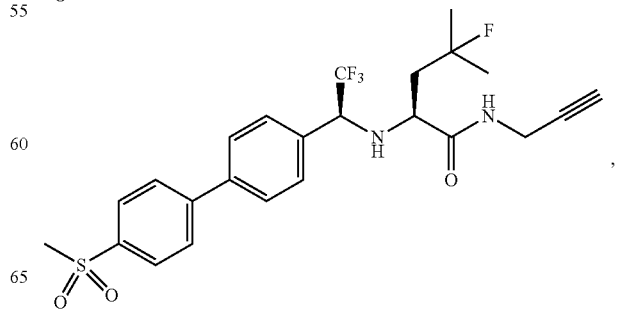

,

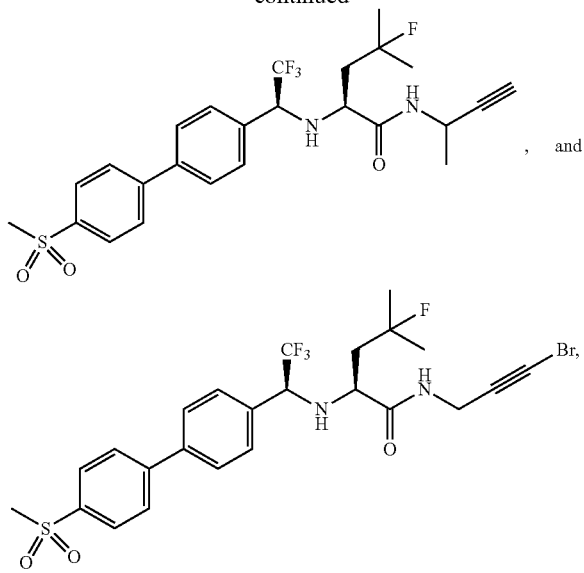

or a pharmaceutically acceptable salt thereof.

17. A composition comprising the compound of claim 1 or a pharmaceutically acceptable salt or mixture thereof, formulated with a pharmaceutically acceptable carrier, an organic bisphosphonate, an estrogen receptor modulator, an estrogen receptor beta modulator, an androgen receptor modulator, an inhibitor of osteoclast proton ATPase, an inhibitor of HMG-CoA reductase, an integrin receptor antagonist, or an osteoblast anabolic agent.

18. A method of inhibiting cysteine-based cathepsin activity, comprising contacting a cysteine-based cathepsin with a compound of claim 1.

19. A method of treating a cysteine-based cathepsin dependent condition in a subject in need thereof, the method comprising administering a therapeutically effective amount of a compound of claim 1 to the subject.

20. The method of claim 19, wherein the condition is selected from osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy or multiple myeloma.

* * * * *